(12) United States Patent
Bagley et al.

(10) Patent No.: US 10,898,263 B2
(45) Date of Patent: *Jan. 26, 2021

(54) UNFURLING ELECTRODE DEVICES

(71) Applicant: COVIDIEN LP, Mansfield, MA (US)

(72) Inventors: Christopher L. Bagley, Santa Clara, CA (US); Allen D. Jameson, Sunnyvale, CA (US); Hillary K. Huszar, Redwood City, CA (US); Mark A. Maguire, Hillsborough, CA (US); David S. Utley, Redwood City, CA (US)

(73) Assignee: Covidien LP, Mansfield, MA (US)

( * ) Notice: Subject to any disclaimer, the term of this patent is extended or adjusted under 35 U.S.C. 154(b) by 430 days.

This patent is subject to a terminal disclaimer.

(21) Appl. No.: 15/899,018

(22) Filed: Feb. 19, 2018

(65) Prior Publication Data

US 2018/0271592 A1    Sep. 27, 2018

Related U.S. Application Data

(63) Continuation of application No. 14/520,028, filed on Oct. 21, 2014, now Pat. No. 9,918,789.

(Continued)

(51) Int. Cl.
*A61B 18/14* (2006.01)
*A61B 18/00* (2006.01)
(Continued)

(52) U.S. Cl.
CPC ............. *A61B 18/1492* (2013.01); *A61B 2017/00871* (2013.01); *A61B 2018/0016* (2013.01);
(Continued)

(58) Field of Classification Search
CPC ........ A61B 18/1492; A61B 2018/0016; A61B 2018/00214; A61B 2018/0022;
(Continued)

(56) References Cited

U.S. PATENT DOCUMENTS

| 4,740,207 A | 4/1988 | Kreamer |
| 4,969,890 A | 11/1990 | Sugita |

(Continued)

FOREIGN PATENT DOCUMENTS

| DE | 102013104948 A1 | 11/2014 |
| EP | 1654980 A1 | 10/2006 |

(Continued)

OTHER PUBLICATIONS

Examination Report for EP Application No. 14190259.3 dated Mar. 11, 2016 from the European Patent Office, Munich Germany.

(Continued)

*Primary Examiner* — Michael F Peffley
(74) *Attorney, Agent, or Firm* — Holland & Hart LLP

(57) ABSTRACT

Methods, systems, and devices for providing treatment to a tissue in body lumens are described. The system may include a catheter, an expansion member coupled with a distal portion of the catheter, an ablation structure including one or more longitudinal electrode segments, and an ablation structure support coupled to the ablation structure configured to at least partially unfurl as the expansion member expands and furl as the expansion member contracts. The ablation structure may include multiple separately wired and/or separately controlled longitudinal electrodes, longitudinal electrode zones, or both, such that each longitudinal electrode or longitudinal electrode zone may be selectively enabled or selectively disabled. In some instances, one or more springs are coupled to the ablation structure configured to promote unfurl or furl around the expansion member. In some instances, one or more protection elements are be positioned along the catheter.

20 Claims, 29 Drawing Sheets

Related U.S. Application Data

(60) Provisional application No. 61/895,501, filed on Oct. 25, 2013, provisional application No. 61/895,514, filed on Oct. 25, 2013, provisional application No. 61/895,530, filed on Oct. 25, 2013.

(51) Int. Cl.
  *A61B 18/12* (2006.01)
  *A61B 17/00* (2006.01)
  *A61M 25/00* (2006.01)

(52) U.S. Cl.
  CPC .......... *A61B 2018/0022* (2013.01); *A61B 2018/00214* (2013.01); *A61B 2018/00285* (2013.01); *A61B 2018/00488* (2013.01); *A61B 2018/00494* (2013.01); *A61B 2018/00577* (2013.01); *A61B 2018/124* (2013.01); *A61B 2018/1465* (2013.01); *A61B 2018/1467* (2013.01); *A61B 2018/1475* (2013.01); *A61B 2018/1495* (2013.01); *A61M 2025/006* (2013.01)

(58) Field of Classification Search
  CPC .......... A61B 2018/00285; A61B 2018/00488; A61B 2018/00494; A61B 2018/00577; A61B 2018/124; A61B 2018/1465; A61B 2018/1467; A61B 2018/1475; A61B 2018/1495; A61B 2017/00871; A61M 2025/006
  See application file for complete search history.

(56) References Cited

U.S. PATENT DOCUMENTS

| | | | |
|---|---|---|---|
| 4,998,539 A | 3/1991 | Delsanti | |
| 5,010,895 A | 4/1991 | Maurer et al. | |
| 5,192,297 A | 3/1993 | Hull | |
| 5,239,999 A * | 8/1993 | Imran | A61B 5/0422 |
| | | | 600/374 |
| 5,462,545 A | 10/1995 | Wang et al. | |
| 5,517,989 A | 5/1996 | Frisbie et al. | |
| 5,533,958 A | 7/1996 | Wilk | |
| 5,716,410 A | 2/1998 | Wang et al. | |
| 5,800,334 A | 9/1998 | Wilk | |
| 5,820,629 A | 10/1998 | Cox | |
| 5,836,874 A | 11/1998 | Swanson et al. | |
| 5,846,196 A | 12/1998 | Siekmeyer et al. | |
| 5,997,534 A | 12/1999 | Tu et al. | |
| 6,006,755 A | 12/1999 | Edwards | |
| 6,016,437 A | 1/2000 | Tu et al. | |
| 6,096,054 A | 8/2000 | Wyzgala et al. | |
| 6,102,908 A | 8/2000 | Tu et al. | |
| 6,123,703 A | 9/2000 | Tu et al. | |
| 6,123,718 A | 9/2000 | Tu et al. | |
| 6,152,899 A | 11/2000 | Farley et al. | |
| 6,156,060 A | 12/2000 | Roy et al. | |
| 6,162,184 A | 12/2000 | Swanson et al. | |
| 6,162,237 A | 12/2000 | Chan | |
| 6,254,598 B1 | 7/2001 | Edwards et al. | |
| 6,258,118 B1 | 7/2001 | Baum et al. | |
| 6,551,310 B1 | 4/2003 | Ganz et al. | |
| 6,752,806 B2 | 6/2004 | Durgin et al. | |
| 6,800,083 B2 | 10/2004 | Hiblar et al. | |
| 6,964,661 B2 | 11/2005 | Rioux et al. | |
| 7,150,745 B2 * | 12/2006 | Stern | A61B 18/06 |
| | | | 606/41 |
| 8,012,149 B2 * | 9/2011 | Jackson | A61M 25/10184 |
| | | | 606/32 |
| 8,192,426 B2 | 6/2012 | Stern et al. | |
| 2002/0065542 A1 | 5/2002 | Lax | |
| 2003/0158550 A1 | 8/2003 | Ganz et al. | |
| 2007/0276361 A1 | 11/2007 | Stevens-Wright et al. | |
| 2008/0249464 A1 | 10/2008 | Spencer et al. | |
| 2008/0319350 A1 * | 12/2008 | Wallace | A61B 5/053 |
| | | | 600/587 |
| 2009/0093802 A1 | 4/2009 | Kulesa | |
| 2014/0378966 A1 | 12/2014 | Haverkost | |
| 2014/0378967 A1 | 12/2014 | Willard | |
| 2015/0119879 A1 | 4/2015 | Jameson et al. | |
| 2015/0119880 A1 | 4/2015 | Huszar et al. | |
| 2015/0119881 A1 | 4/2015 | Bagley et al. | |

FOREIGN PATENT DOCUMENTS

| | | |
|---|---|---|
| EP | 2604212 A1 | 6/2013 |
| JP | 2014530644 | 11/2014 |
| JP | 2014530644 A | 11/2014 |
| WO | 0128446 A1 | 4/2001 |
| WO | 2005067668 A2 | 7/2005 |
| WO | 2008061528 A1 | 5/2008 |
| WO | WO-2013028998 A2 | 2/2013 |

OTHER PUBLICATIONS

Notice of Reasons for Rejection for Japanese Patent Application No. 2014-53066, dated Apr. 5, 2017, from the Japanese Patent Office.
Extended European Search Report dated Mar. 5, 2015 for Application No. 14190259.3 from European Patent Office, pp. 1-4.
Extended European Search Report dated Jun. 14, 2016 for Application No. 15191980.0 from European Patent Office.
Extended European Search report dated Jun. 22, 2016 for Application No. 15202393.3 from European Patent Office.
Notification of the First Office Action dated Aug. 21, 2017 for Application No. 201510845131.4 from State Intellectual Property Office of the People's Republic of China.
Chinese Office Action dated Oct. 10, 2017 for Application No. 201610068875.4 from the Chinese Patent Office.
Canadian Office Action for CA Patent Appliction No. 2,910,361 dated Sep. 27, 2016, from the Canadian Intellectual Property Office.
Patent Examination Report No. 1 for Patent Application No. 2015249116 dated Oct. 20, 2016, from the Australian Government.
Office Action fro the Canadian Intellectual Property Office dated Mar. 21, 2017 for Application No. 2,917,513.
Notice of Reasons for Rejection for JP Application No. 2018-225156, dated Oct. 2, 2019, 4 pgs., Japan Patent Office (JPO).

* cited by examiner

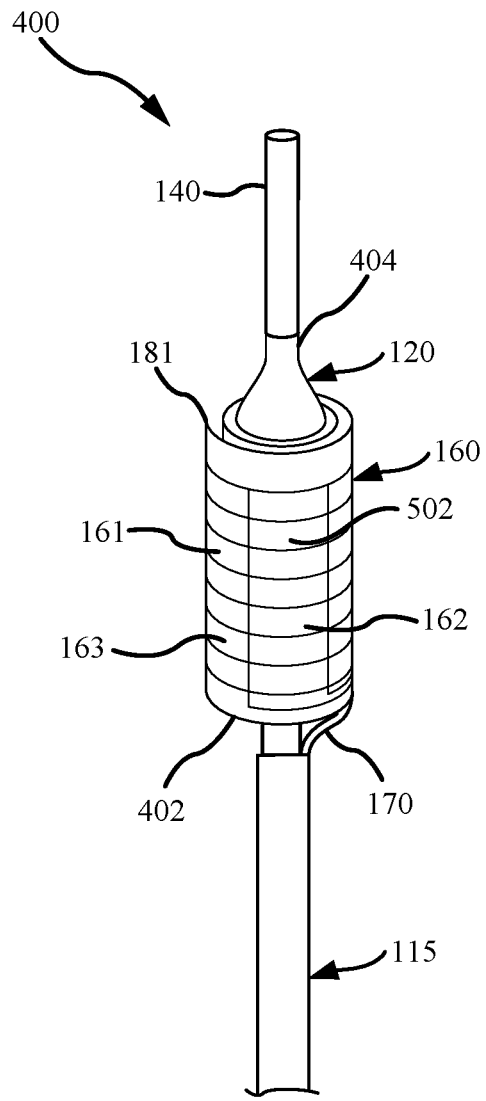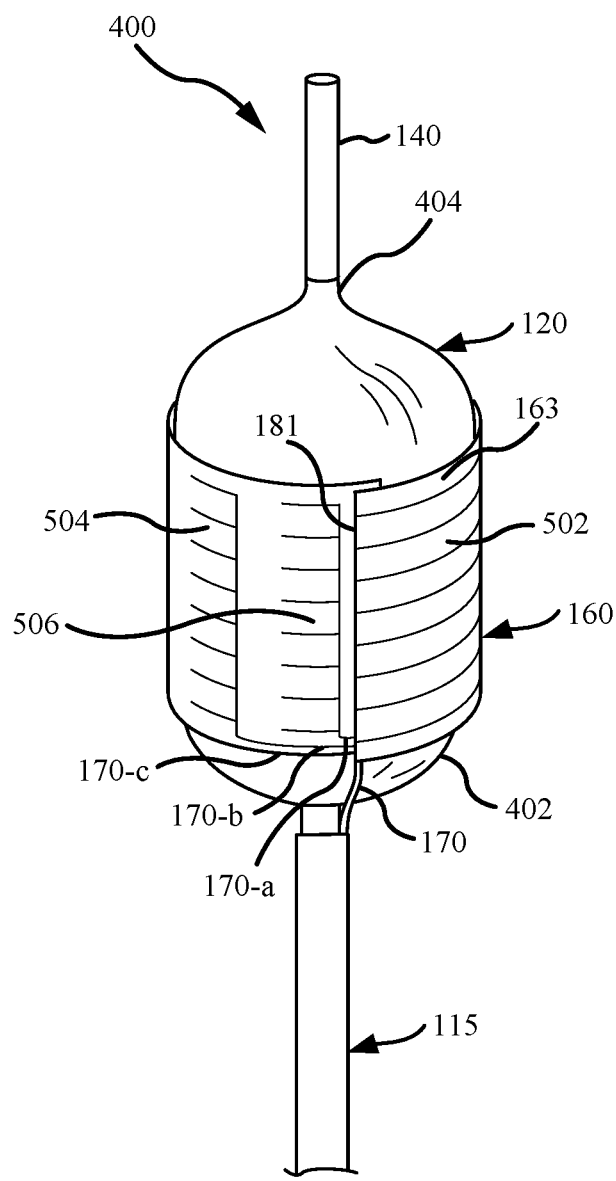
FIG. 4
FIG. 5

UNFURLING ELECTRODE DEVICES

CROSS REFERENCES

This application is a continuation of prior U.S. patent application Ser. No. 14/520,028, filed on Oct. 21, 2014, now U.S. Pat. No. 9,918,789, entitled "UNFURLING ELECTRODE DEVICES WITH THE PROTECTION ELEMENT", and claims the benefit of and priority to U.S. Provisional Application No. 61/895,501, filed on Oct. 25, 2013, entitled, "UNFURLING ELECTRODE DEVICES WITH THE MULTIPLE LONGITUDINAL ELECTRODE SEGMENTS"; U.S. Provisional Application No. 61/895,514, filed Oct. 25, 2013, entitled, "UNFURLING ELECTRODE DEVICES WITH SPRING"; and U.S. Provisional Application No. 61,895,530, filed on Oct. 25, 2013, entitled, "UNFURLING ELECTRODE DEVICES WITH THE PROTECTION ELEMENT", each of which are incorporated by reference in their entirety for all purposes. This application is also related to U.S. patent application Ser. No. 14/519,409, filed Oct. 21, 2014, entitled "UNFURLING ELECTRODE DEVICES WITH THE MULTIPLE LONGITUDINAL ELECTRODE SEGMENTS;" and U.S. patent application Ser. No. 14/519,950, filed Oct. 21, 2014, entitled, "UNFURLING ELECTRODE DEVICES WITH SPRING," each of which are incorporated by reference in their entirety for all purposes.

BACKGROUND

The human body has a number of internal body lumens or cavities located within, such as the differing parts of the gastro-intestinal tract, many of which have an inner lining or layer. Body lumens may include, for example, the esophagus, small and large intestines, stomach, remnant after bariatric surgery, rectum and anus. These inner linings may be susceptible to disease. In some cases, different ablation techniques have been utilized with respect to the inner lining in order to prevent the spread of disease to otherwise healthy tissue located nearby.

Internal body lumens may have different sizes with respect to each other or with respect to different patients. As a result, different sized devices may have been utilized to accommodate these different sized lumens. However, this may involve utilizing multiple devices such as multiple sizing and/or treatment devices, which may not be as efficient, cost effective, or safe as a device that can both size and treat with a single intubation.

Another problem may exist when treating a target site larger than the surface area of the treatment device. Conventional ablation approaches often involved three or more repositioning steps in order to treat a target site. Such repositioning activities may be susceptible to decreased accuracy of treatment, over or under ablation of subregions of the target site, or both. In addition, repositioning activities may be ad hoc with respect to the number of repositioning steps and the physical processes associated with the actual repositioning of the device. Such lack of consistency may further decrease accuracy of treatment, efficiency of treatment, or both.

There may thus be a need for systems, devices and methods that may overcome the above and/or other disadvantages of known systems, devices, and methods.

SUMMARY

Methods, systems, and devices are described for providing treatment to a target site, such as a site within a body lumen. Systems may include an expansion member coupled with a distal portion of a catheter, and an ablation structure support coupled to an ablation structure configured to at least partially furl and unfurl around the expansion member as the expansion member expands and contracts. The expansion member may include a non-compliant, compliant, or highly-compliant balloon. The ablation structure support may include one or more longitudinal electrodes, longitudinal electrode zones, and/or longitudinal electrode regions. In some embodiments, the system may include one or more protection elements positioned along the catheter distal to the ablation structure, proximal to the ablation structure, or both.

According to some embodiments of the disclosure, an ablation device for treatment of tissue in body lumens with varying sizes is provided. The ablation device generally includes an expansion member coupled with a distal portion of a catheter, and an ablation structure including a number of longitudinal electrode regions. An ablation structure support may be coupled with the ablation structure and the ablation structure and the ablation structure support may be configured to at least partially unfurl or furl around the expansion member as the expansion member expands or contracts.

In some embodiments, the ablation device further includes one or more springs coupled with the ablation structure support configured to furl the ablation structure support at least partially around the expansion member. The one or more springs may include one or more constant force springs. The ablation device may also include one or more protection elements positioned along the catheter at least distal or proximal to the ablation structure.

In some embodiments, each of the longitudinal electrode regions of the ablation device is configured to be selectively enabled or disabled. Each of the longitudinal electrode regions may be controlled or wired separately. In certain embodiments, the longitudinal electrode regions include at least two longitudinal electrode regions with different widths. The ablation device may include at least one bipolar electrode array in some embodiments. In certain instances, the expansion member is a balloon, and the balloon may be compliant in some embodiments.

According to some embodiments of the disclosure, a method for treatment of tissue in body lumens with varying sizes is provided. The method generally includes inserting an ablation structure coupled with an ablation structure support and an expansion member into a body lumen. The ablation structure and the ablation structure support may be configured to at least partially unfurl or furl around the expansion member as the expansion member expands or contracts. The method further includes expanding the expansion member to at least partially unfurl the ablation structure to engage a circumferential section of the body lumen, and delivering energy through one or more of a plurality of longitudinal electrode regions of the ablation structure to the circumferential section of the body lumen.

In some instances, delivering energy through one or more of the plurality of longitudinal electrode regions of the ablation structure to the circumferential section of the body lumen includes selectively enabling each of the longitudinal electrode regions. The method may further include contracting the expansion member to facilitate removing the ablation structure from the body lumen. In some embodiments, one or more springs cause the ablation structure to furl at least partially around the expansion member as the expansion member contracts. The one or more springs may include one or more constant force springs in some instances.

In certain embodiments, the method further includes utilizing one or more protection elements with respect to at least a distal portion or a proximal portion of the ablation structure while inserting the ablation structure coupled with the ablation structure support and the expansion member into the body lumen. In some embodiments, the method further includes moving the one or more protection elements away from the ablation structure after positioning the ablation structure in the body lumen. In certain instances, the method further includes determining an impedance for each of the plurality of longitudinal electrode regions of the ablation structure, and comparing the determined impedances to determine whether one or more of the longitudinal electrode regions is at least partially covered by an electrode segment.

In some embodiments, the longitudinal electrode regions of the ablation structure include at least two longitudinal electrode regions with different widths. The ablation structure may include at least a bipolar electrode array in certain instances. The expansion member may be a balloon in some embodiments.

According to some embodiments of the disclosure, an ablation device for treatment of tissue in body lumens with varying sizes is provided. The ablation device generally includes an expansion member coupled with a distal portion of a catheter and an ablation structure configured to at least partially unfurl or furl around the expansion member as the expansion member expands or contracts. The ablation device further includes one or more springs, coupled with the ablation structure, and configured to provide a force to cause the ablation structure to unfurl or furl around the expansion member as the expansion member expands or contracts.

In some embodiments, the one or more springs of the ablation device includes one or more strips of material coupled with the ablation structure laterally with respect to a longitudinal axis of the ablation structure. In certain instances, the one or more springs of the ablation device includes one or more strips of material such that a density of the one or more strips of material proximal to a free end of the ablation structure is less than a density of the one or more strips of material distal to the free end of the ablation structure. In yet other embodiments, the one or more springs of the ablation device include one or more strips of material such that a density of the one or more strips of material proximal to a free end of the ablation structure and proximal to a mounted end of the ablation structure is less than a density of the one or more strips of material at a middle portion of the ablation structure. The one or more strips of material may include a metallic material or a polymer material. The one or more strips of material may include a shape memory polymer material in some embodiments.

In certain instances, the one or more springs of the ablation device includes at least a first spring with a first length and a second spring with a second length different from the first length. The first length may be greater than the second length and the second spring with the second length may be positioned distal to the free end of the ablation structure.

In some embodiments, the one or more strips of material of the one or more springs includes one or more rectangular strips of material. In certain instances, at least one of the rectangular strips of material includes one or more openings configured into at least one end of the at least one rectangular strips. In some embodiments, at least one of the strips of material includes at least a tapered portion. In yet other embodiments, at least one of the strips of material includes one or more slots configured into at least one end of the at least one strip of material.

In certain embodiments, the ablation structure of the ablation device includes a number of longitudinal electrode regions where the longitudinal electrode regions are configured to be sequentially activated. In some embodiments, the ablation structure includes a number of longitudinal electrode regions where the longitudinal electrode regions are configured to be sequentially activated beginning with a first electrode region adjacent to a free end of the ablation structure. In yet some other embodiments, the ablation structure includes a number of longitudinal electrode regions where each longitudinal electrode region is configured to be selectively enabled or disabled. The longitudinal electrode regions may include at least two longitudinal electrode regions with different widths. In certain instances, the at least two longitudinal electrode regions of different widths include a first longitudinal electrode region adjacent to a free end of the ablation structure and a second longitudinal electrode region, where the first longitudinal electrode region has a width greater than the width of the second longitudinal electrode region.

In some embodiments, the longitudinal electrode regions of the ablation device include at least three longitudinal electrode regions with different widths comprising a first longitudinal electrode region proximal to a free end of the ablation structure, a second longitudinal electrode region adjacent to the first longitudinal electrode region, and a third longitudinal electrode region distal to the free end of the ablation structure. The first longitudinal electrode region may have a width greater than the width of the second longitudinal electrode region and the second longitudinal electrode region may have a width greater than the width of the third longitudinal electrode region.

In certain embodiments, the ablation structure of the ablation device includes at least a bipolar electrode array. In some embodiments, the expansion member of the ablation device is a balloon.

According to embodiments of the disclosure, an ablation device for treatment of tissue in body lumens with varying sizes is provided. The ablation device generally includes an ablation structure coupled with a catheter including one or more protection elements positioned along the catheter distal to the ablation structure, proximal to the ablation structure, or both. In some embodiments, the ablation structure includes a furled bi-polar electrode array.

In some instances, the one or more protection elements include one or more cones configured to protect one or more edges of the ablation structure. The one or more cones may each have a base circumference greater than a circumference of the collapsed ablation structure. Furthermore, the one or more cones may be configured to move away from the ablation structure when the ablation structure is deployed to engage the tissue. In some embodiments, the ablation device may further include one or more tethers configured to facilitate moving the one or more cones with respect to the ablation structure.

In certain instances, the one or more protection elements are configured to prevent the ablation structure from distending along the catheter during at least deployment into a body lumen or removal from the body lumen. The one or more protection elements may be configured to prevent the ablation structure from damaging a surface of a body lumen during at least deployment into the body lumen or removal from the body lumen.

In some embodiments, the one or more protection elements include one or more bumpers coupled with one or more edges of the ablation structure. The one or more bumpers may overhang the edge of the ablation structure inwards towards the catheter.

According to various embodiments, the one or more protection elements proximal to the ablation structure may include a raised bump coupled with the catheter. The raised bump may be configured to prevent the ablation structure from distending proximally along the catheter during insertion or deployment into a body lumen.

In various embodiments, the ablation device further includes an expansion member coupled with the catheter wherein the ablation structure is furled around the expansion member. In such embodiments, the one or more protection elements distal to the ablation structure may include a portion of the expansion member configured to bunch up when the expansion member is unexpanded such that a diameter of the bunched up portion exceeds a diameter of the furled ablation structure. The bunched up portion of the expansion member may be configured to prevent the ablation structure from distending distally along the catheter during removal from a body lumen.

In certain instances, the one or more protection elements include a first protection element positioned distal to the ablation structure with respect to the catheter and a second protection element positioned proximal to the ablation structure with respect to the catheter.

In accordance with some embodiments of the present disclosure, a method for treatment of tissue in body lumens with varying sizes is provided. The method generally includes inserting an ablation structure coupled with a catheter into a body lumen. One or more protection elements may be positioned along the catheter at least distal or proximal to the ablation structure. The method further includes expanding an expansion member to at least partially unfurl the ablation structure to engage the body lumen. The protection elements may include one or more cones configured to protect one or more edges of the ablation structure. In some instances, the method further includes displacing the one or more cones away from the ablation structure when the ablation structure is deployed to engage the body lumen. The method may further include utilizing one or more tethers coupled with the one or more protection elements to facilitate moving the one or more protection elements with respect to the ablation structure.

In some instances, the one or more protection elements are configured to prevent the ablation structure from distending along the catheter during deployment into the body lumen. In certain embodiments, the one or more protection elements include one or more bumpers coupled with one or more edges of the ablation structure. The one or more bumpers may overhang the edge of the ablation structure inwards towards the catheter.

According to various embodiments, the one or more protection elements proximal to the ablation structure may include a raised bump coupled with the catheter. The raised bump may be configured to prevent the ablation structure from distending proximally along the catheter during deployment or insertion into the body lumen.

In certain instances, the one or more protection elements distal to the ablation structure may include a portion of the expansion member configured to bunch up when the expansion member is unexpanded such that a diameter of the bunched up portion exceeds a diameter of the furled ablation structure. The bunched up portion of the expansion member may be configured to prevent the ablation structure from distending distally along the catheter during removal from a body lumen.

In some embodiments, the one or more protection elements include a first protection element positioned distal to the ablation structure with respect to the catheter and a second protection element positioned proximal to the ablation structure with respect to the catheter.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the spirit and scope of the appended claims. Features which are believed to be characteristic of the concepts disclosed herein, both as to their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWING

A further understanding of the nature and advantages of the embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 4 is a perspective view of an ablation device, in a furled/collapsed mode, coupled with multiple separately-wired longitudinal electrode zones.

FIG. 5 is a perspective view of an ablation device, in an unfurled/expanded mode, coupled with multiple separately-wired longitudinal electrode zones.

DETAILED DESCRIPTION

Figure 1A:
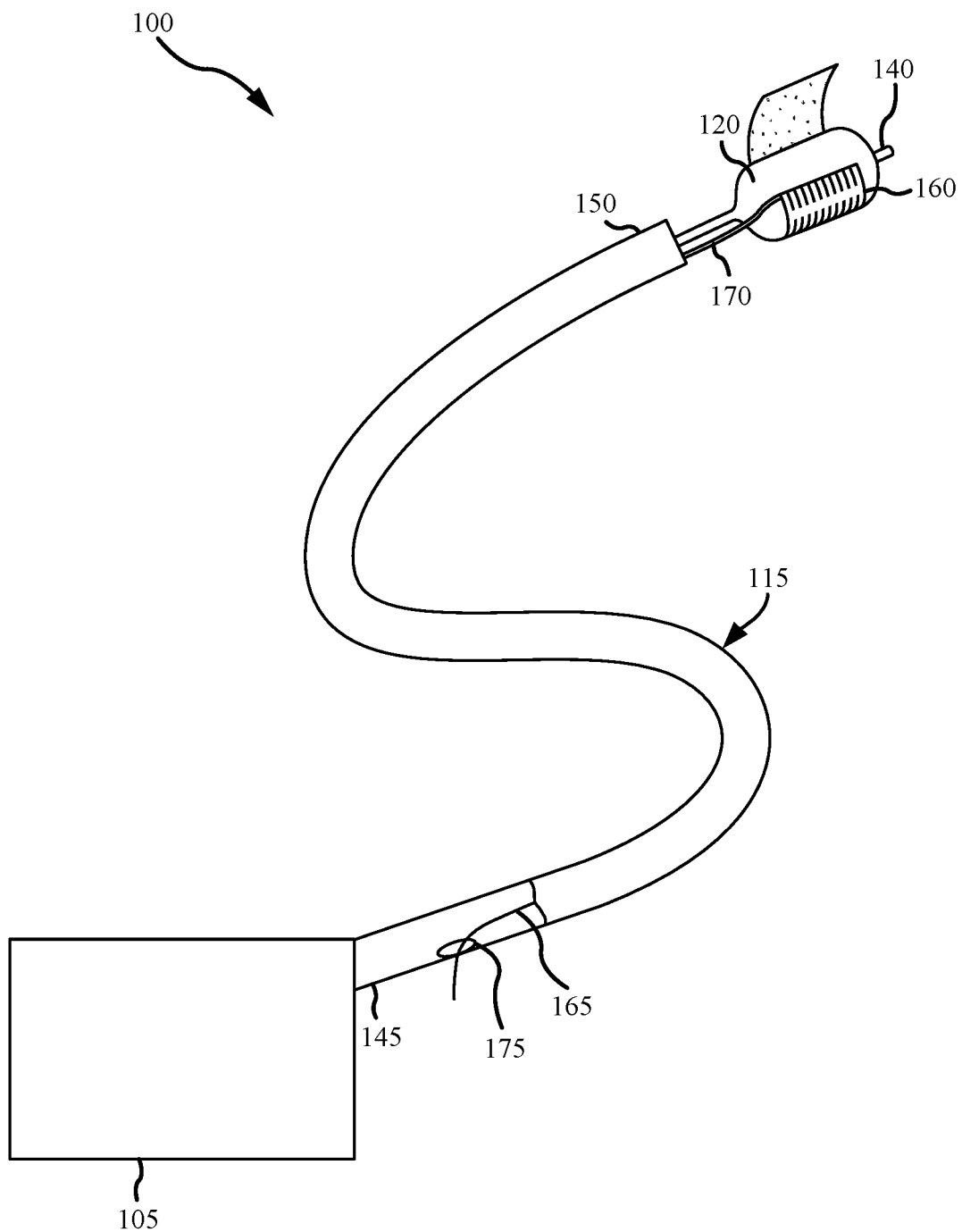
FIG. 1A is a schematic diagram of a system for delivering treatment to a target treatment area including components configured according to various embodiments.

Methods, systems, and devices are described for providing treatment to a target site, such as a site within a body lumen. Systems may include an expansion member that may be coupled with a distal portion of a catheter. An ablation structure may be wrapped around the expansion member such that expanding the expansion member may engage body lumens of varying sizes.

An ablation structure support coupled to an ablation structure may be positioned at a distal end of a catheter. The ablation structure may include a flexible circuit capable of furling and unfurling around an expansion member upon which it may be disposed. Various aspects of the flexible circuit may be similar to typical integrated circuits and microelectronic devices. The flexible circuit may include multiple separately wired or separately controlled longitudinal electrodes, longitudinal electrode zones, or both, aligned in parallel to an axis about which the ablation structure transitions between a furled configuration and an unfurled configuration.

The ablation structure may include longitudinal electrodes of varying widths, longitudinal electrode zones of varying widths, or both. Each longitudinal electrode or longitudinal electrode zone may be selectively enabled or selectively disabled. For purposes of this application, enabling an electrode or electrode zone has the same meaning as activating an electrode or electrode zone. In some instances, the ablation structure includes an electrode array, such as, for example, a bipolar electrode array.

The ablation structure support may be coupled to one or more springs. Springs may be made of various materials such as, for example, a metallic material or a polymer material. The positional density of the springs relative to the ablation structure support may vary such that clawing effects are reduced at one or more ablation structure locations. Spring density may be varied by structures that include, for example, slotted springs, tapered springs, and/or variable-length springs.

One or more protective elements may be positioned along the catheter distal to the ablation structure and/or proximal to the ablation structure. Slidably movable conical protection elements may be positioned such that they cover the edges of the ablation structure support, preventing scraping of the lumen or ablation support structure distension during insertion and removal. The distal end of a tethering structure may be mounted to the conical protection elements such that the protection elements may be moved upon deployment of the expansion member, removing the cones from obstructing the furling and unfurling transitions. In some cases, a flexible distal protective bumper element less than the circumference of the furled ablation structure is coupled with the longitudinal edge of the distal lateral portion of the ablation structure. The furled ablation structure including the protective bumper element may resemble the familiar tubular shape of an endoscope. Additionally, the catheter may include a raised bump positioned proximal to the ablation structure configured to prevent distention of the ablation structure along the catheter during insertion of the ablation structure into a body lumen. Moreover, the expansion member may include a portion distal to the ablation structure that bunches up when the expansion member is unexpanded such that the bunched up expansion member material prevents distension of the ablation structure along the catheter during removal of the ablation structure from a body lumen.

With reference to FIG. 1A, a general system 100 for delivering treatment to a target treatment area is shown in accordance with various embodiments. The system 100 may be designed for providing treatment to a target area inside of a body, such as the wall of an organ or lumens in the gastrointestinal tract, for example. The system 100 may include a power source 105, a catheter 115, and an expansion member 120. The expansion member 120 may generally be configured to support an ablation structure 160 that may be used to supply therapy to the target treatment site. The system 100 may operate by positioning a guide assembly 165 inside a body and passing the expansion member 120 over the guide assembly 165 such that the expansion member 120 may be delivered to a target treatment site inside the body. The power source 105 may then be used to supply power to an ablation structure 160 disposed on the expansion member 120 so that therapy may be applied to the target treatment site.

The expansion member 120 may be an inflatable device capable of transitioning between a collapsed or unexpanded configuration and an expanded configuration with the use of a supplementary expansion mechanism. Suitable expansion members 120 include but are not limited to a balloon, compliant balloon, balloon with a tapered geometry, bladder, and the like. In some embodiments, the power source 105 is configured to inflate the expansion member 120 by, for example, incorporating the supplementary expansion mechanism internally. The collapsed configuration may be generally used when the expansion member 120 is inserted into and removed from the body lumen. When the expansion member 120 obtains a desired ablation position, the expansion member 120 may expand, such as by inflating from a deflated state (i.e. the collapsed configuration) to a substantially inflated state (i.e., the expanded configuration).

The expansion member 120 may be configured to support an ablation structure 160. In some embodiments, the ablation structure 160 is a therapeutic or diagnostic instrument, such as an ablation element that may provide ablative energy to the target treatment area. Some ablation structures 160 may be designed so that they make direct contact with a target treatment area, including pressing of the ablation structure 160 against the target site.

The expansion member 120 may be coupled with the catheter 115 such that the expansion member 120 may be maneuvered through a channel of the body, such as the esophagus, and at the target treatment area. The catheter 115 may be coupled with the power source/inflation device 105 at the proximal end 145 of catheter 115. The expansion member 120 may be positioned between the distal end 140 of the catheter 115 and a portion 150 of the catheter 115. In some embodiments, the catheter 115 includes an opening 175 configured to allow the entry and exit of the guide assembly 165 such that the catheter 115 is slidably movable relative to the guide assembly 165. The guide assembly entry point 175 may typically be located outside of the catheter 115 and proximate the power source 105.

The power source 105 may provide power to the ablation structure 160 disposed on the expansion member 120. In some embodiments, power is provided from the power source 105 to the ablation structure 160 via one or more transmission lines 170 extending between the power source 105 and the ablation structure 160 and housed within a channel of the catheter 115.

Figure 1B:
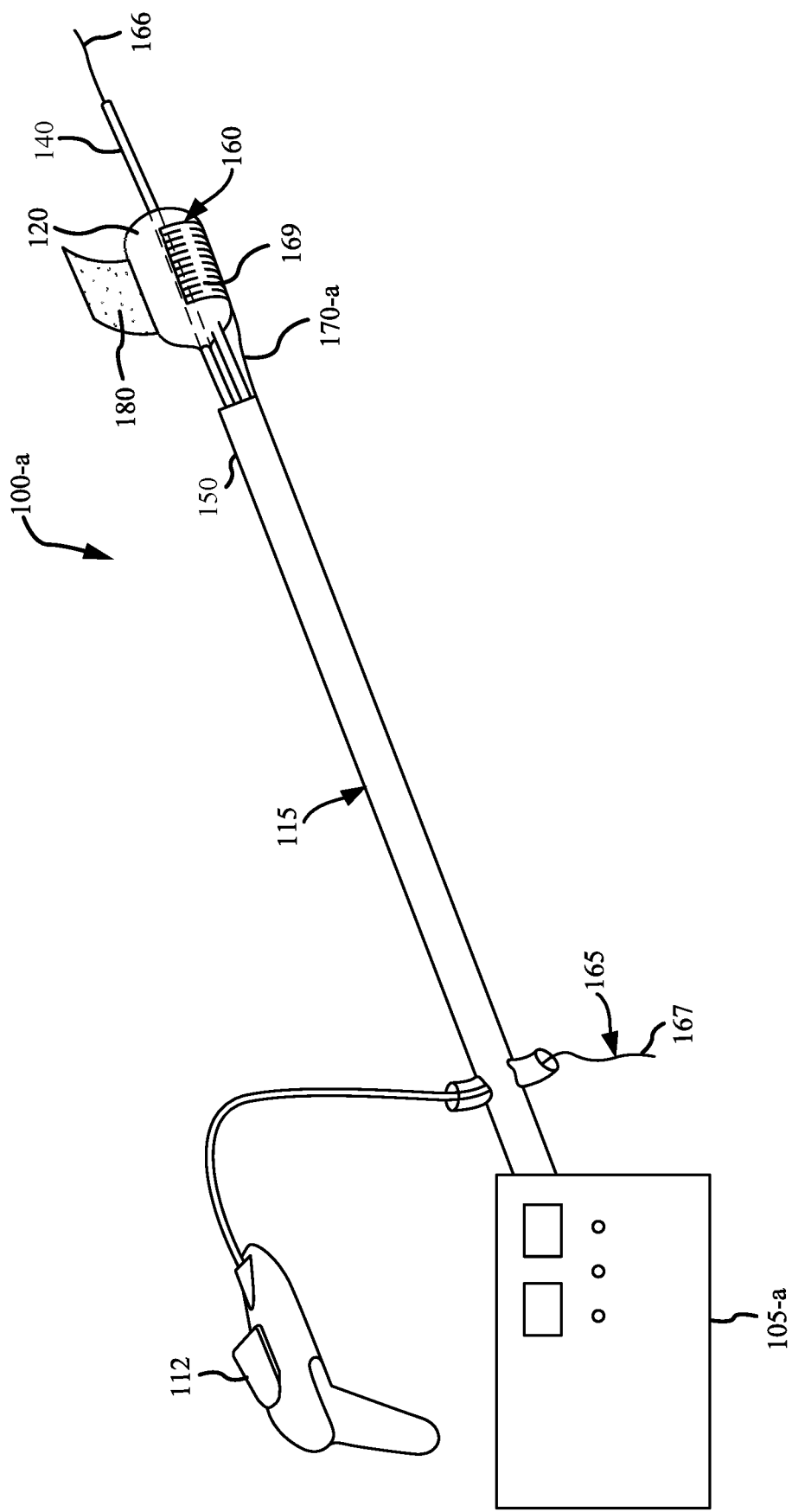
FIG. 1B is schematic diagram of one specific embodiment of the system shown in FIG. 1A.

FIG. 1B illustrates a system 100-*a* that may be an example of the system 100 shown in FIG. 1A according to various embodiments. The system 100-*a* may include a generator 105-*a*, a hand-held air compressor 112, a guide assembly 165 with a distal end 166 and a proximal end 167, a catheter 115, an expansion member 120, an ablation structure 160, and/or an ablation structure support 180 coupled with the expansion member 120.

The expansion member 120 may include a balloon on which the ablation structure support 180 may be supported. The expansion member 120 may be a flexible material capable of being curved or folded that, when expanded, generally may have an elongated cylindrical shape, including a rounded distal end. The expansion member 120 may taper at its proximal end and couple with the catheter 115 near portion 150 of catheter 115.

Disposed on a portion of the surface of the expansion member 120 may be an ablation structure 160 configured to provide treatment to the target treatment area. The ablation structure 160 may include a single electrode including multiple electrode zones or a series of electrodes 169 laterally adjacent to one another and parallel to the longitudinal axis of the ablation structure 160 and expansion member 120. The one or more electrodes 169 may be interlaced, with approximately half of the electrodes extending from a first bus and approximately half of the electrodes extending from a second bus. The first bus or the second bus may be connected to a positive terminal and the other of the first bus or the second bus may be connected to a negative or ground terminal to thereby provide a bipolar electrode configuration. When connected to the power source 105-*a*, the one or more electrodes 169 may provide ablative energy to the target treatment area.

The expansion member 120 may be coupled with a portion 150 of the catheter 115 that is proximate to the distal end 140 of catheter 115. The ablation structure support 180 may be furled at least partially around the outside circumference of the expansion member 120 such that when the expansion member 120 expands, the ablation structure support 180 adapts to the changing circumference while the ablation structure 160 maintains a constant electrode density per unit area. A set of transmission wires 170-*a* may extend from the power source 105-*a* to the ablation structure 160 through the channel of the catheter 115. Zone activation may be controlled from the power source 105-*a* and/or from a switching printed circuit board configured to drive one or more additional channels.

Figure 1C:
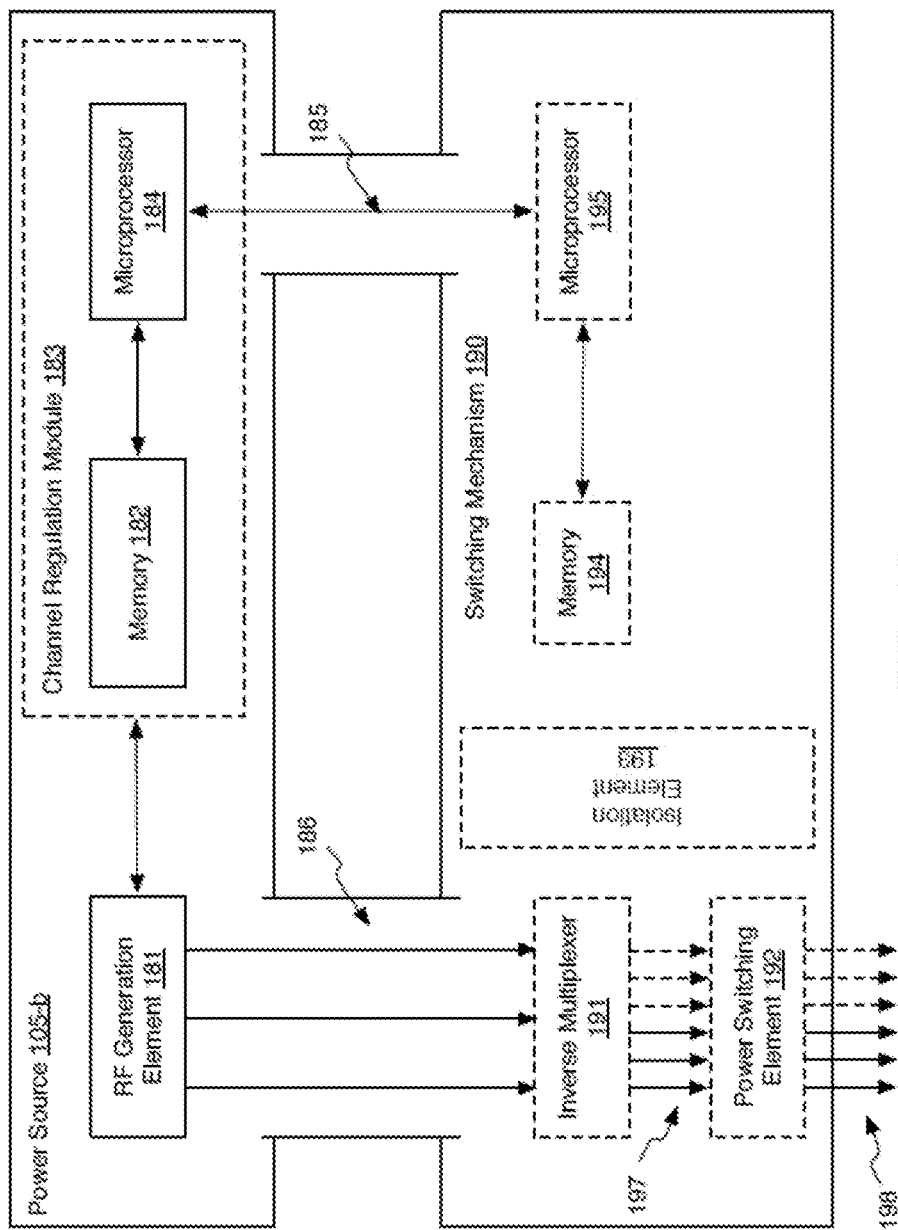
FIG. 1C is a schematic diagram of a power source and a switching mechanism of the system shown in FIG. 1A and FIG. 1B.

With reference now to FIG. 1C, a power source 105-*b* is schematically illustrated in accordance with various embodiments. Power source 105-*b* may be an example of power source 105 or 105-*a* described with reference to FIG. 1A or 1B. In general, the power source 105-*b* may include a power switching mechanism 190 which may be configured to switch on and switch off longitudinal electrode regions, thus controlling, at least in part, the order, timing, and duration of energy delivery at the treatment site. For example, the power switching mechanism 190 may include an RF generation element 181, which may be configured to transmit RF energy on one or more output channels 186 to a power switching element 192 where such power switching element 192 then reroutes the RF energy 198 to multiple longitudinal electrode regions. In some implementations, the power switching mechanism 190 is an external component communicatively coupled to the power source 105-*b* and the catheter 115. In other cases, the power switching mechanism 190 is integral to and/or attached to the catheter 115. In certain instances, the combined catheter 115 and switching mechanism 190 components are single-use disposable components.

In some cases, the number of defined longitudinal electrode regions of the ablation structure 160 is less than or equal to the number of RF channels 186 supported by the power source 105-*b*, with each defined longitudinal electrode region coupled to a single RF channel 186. In such a configuration, the switching mechanism 190 may be communicatively coupled with a channel regulation module 183 integrated with the power source 105-*b*. The channel regulation module 183 may include a microprocessor 184 and a memory 182. The switching mechanism 190 may also include a microprocessor 195 and a memory 194. The channel regulation module 183 may direct the switching mechanism 190 to either enable or disable the RF channel 186 associated with one or more electrode regions in accordance with one or more algorithms stored in memory 182. In some instances, the switching mechanism 190 may communicate ablation parameters such as, for example, impedance to the power source 105-*b* for use in algorithmic determinations.

In certain implementations, the number of defined electrode regions exceeds the number of RF channels 186 supported by the power source 105-*b*. For example, an RF generation element 181 may support a maximum of 3 RF channels 186, where the ablation structure 160 (see e.g., FIG. 1) may include 6 separately-wired electrode regions. In such cases, the RF generation element 181 may be configured to transmit RF energy on only one output channel 186 to the power switching element 192, where such power switching element 192 then reroutes the RF energy to multiple longitudinal electrode regions. Alternatively, the RF generation element 181 may be configured to transmit RF energy over multiple output channels 186 to an inverse multiplexer 191, where such inverse multiplexer 191 expands the number of channels 197 by, for example, re-routing the common return of the bipolar system.

Additionally, or alternatively, the power source 105-*b* may be configured to transmit RF energy across one or more channels 186 concurrently or in a defined sequence. In some embodiments, the switching mechanism 190 switches RF output channels 186 on or off by blocking the transmission from the RF generation element 181. The switching mechanism 190 may include a power-switching element 192 such as, for example, a metal-oxide-semiconductor field-effect transistor or a relay. In some instance, an isolation element 193 is positioned between the power switching element 192 and the logic element or microprocessor 195 and memory 194. In some instances, the channel regulation module 183 communicates a longitudinal electrode region activation sequence to the power switching element 192 that either blocks or allows RF transmission in accordance with the received sequence, thus controlling the activation, timing, and or duration of energy delivery at the longitudinal electrode regions associated with the RF channels 186. Additionally, or alternatively, the switching mechanism 190 may determine the longitudinal electrode region activation sequence independent of the power source 105-*b* based, at least in part, on an algorithm stored in memory 194.

In some instances, the switching mechanism 190 monitors current and/or interprets other signals communicated from the power source 105-*b* to determine, in part, when to switch a channel on or off. Additionally, or alternatively, the power source 105-*b* may control the switching behavior of the switching mechanism 190 via a one-way or two-way communication channel 185 coupling the power source logic element 184 and the switching mechanism logic element 195. In certain implementations, the power source 105-*b* may receive feedback from the switching mechanism 190, such as, for example, an acknowledgment that switching instructions were received and/or that the directed switching behavior was executed. Communication between the logic elements 184, 195 may implement an established communication protocol such as, for example, I2C or SPI.

The ablation of tissue may result in a variation to the impedance of that tissue as compared to unablated tissue. A probe sensor may be used to determine the ablation condition of regions of the circumferential treatment site by, for example, comparing the impedance of a region of a treatment site with previous impedance data for the same and/or different regions of a treatment site. This data may then be used to select the activation state and/or activation duration for one or more longitudinal electrode regions. It will be appreciated by one skilled in the art that these and other automated selection algorithms may be implemented on one or more communicatively coupled computer devices external to the power source 105-*b*. For example, additional computer software, such as image analysis software, may be used to identify previously ablated regions and/or overlapping electrode segments as part of an algorithm that regulates the activation and/or energy delivery profile of the associated electrode regions.

Figure 2:
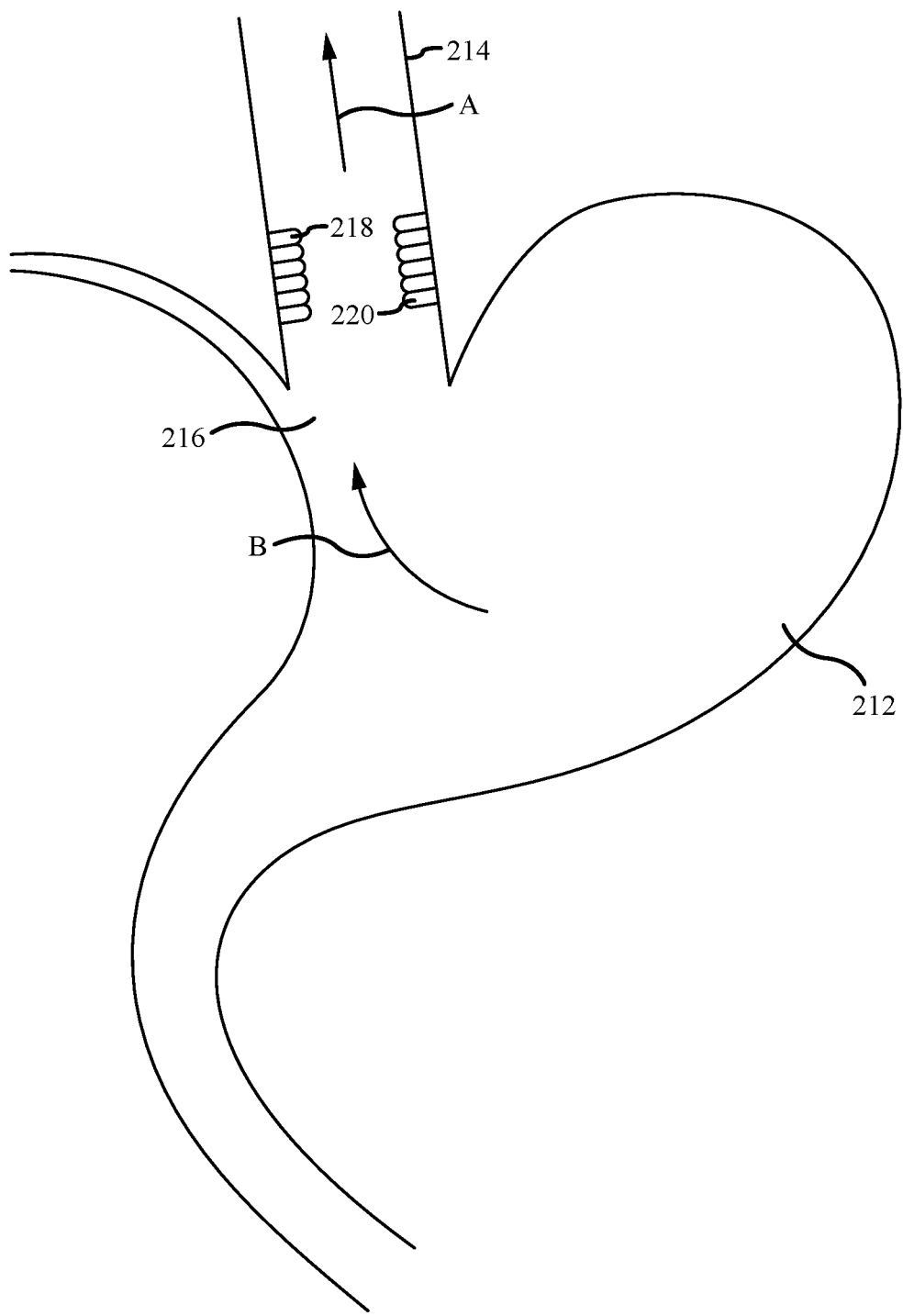
FIG. 2 is a schematic view of portions of an upper digestive tract in a human.

Referring now to FIG. 2, certain disorders may cause the retrograde flow of gastric or intestinal contents from the stomach 212, into the esophagus 214, as shown by arrows A and B. Although the causes of these problems are varied, this retrograde flow may result in secondary disorders, such as Barrett's esophagus, which require treatment independent of and quite different from treatments appropriate for the primary disorder—such as disorders of the lower esophageal sphincter 216. Barrett's esophagus is an inflammatory disorder in which the stomach acids, bile acids and enzymes regurgitated from the stomach and duodenum enter into the lower esophagus causing damage to the esophageal mucosa. When this type of retrograde flow occurs frequently enough, damage may occur to esophageal epithelial cells 218. In some cases, the damage may lead to the alteration of the squamous cells, causing them to change into taller specialized columnar epithelial cells 220. This metaplastic change of the mucosal epithelium from squamous cells to columnar cells is called Barrett's esophagus. Although some of the columnar cells may be benign, others may result in adenocarcinoma.

In some embodiments, the methods, systems, and devices described are configured to treat columnar epithelium of selected sites of the esophagus through the ablation of the tissue. The term "ablation" as used herein means thermal damage to the tissue causing tissue or cell necrosis. It will be appreciated by one skilled in the art that some therapeutic procedures may have a desired treatment effect that falls short of ablation, such as, for example, some level of agitation or damage that may be imparted to the tissue to insure a desired change in the cellular makeup of the tissue, rather than necrosis of the tissue. In some instances, a variety of different energy delivery devices are utilized to create a treatment effect in a superficial layer of tissue, while preserving intact the function of deeper layers, as described hereafter.

Cell or tissue necrosis may be achieved with the use of energy, such as RF energy, at appropriate levels to accomplish ablation of mucosal or submucosal level tissue, while substantially preserving muscular is tissue. Such ablation may be utilized to remove the columnar growths 220 from the portions of the esophagus 214 so affected.

Figure 3A:
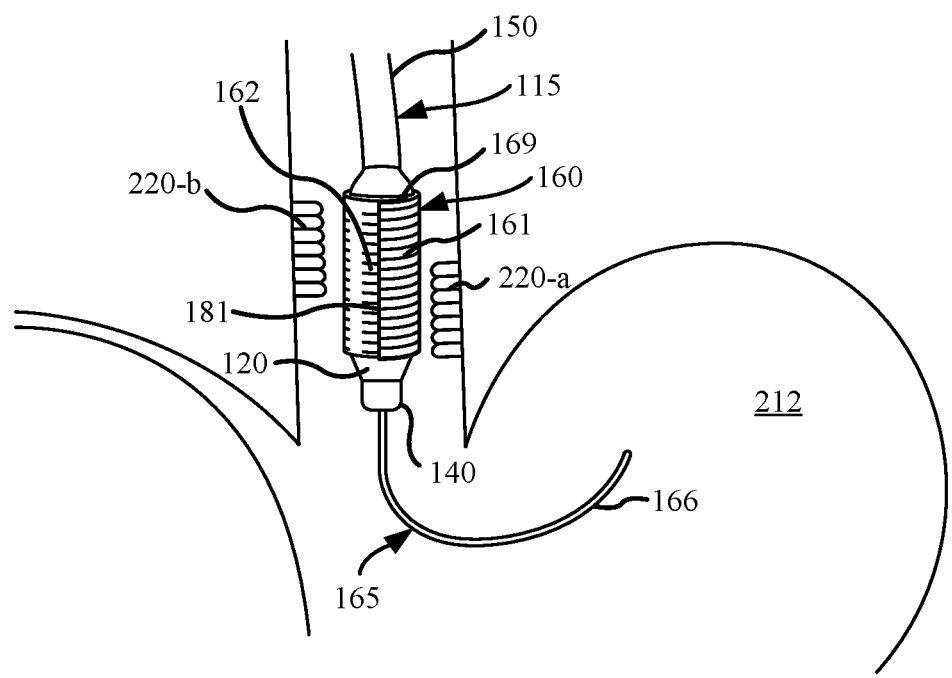
FIG. 3A is a schematic view of an ablation device, in a furled/collapsed mode, within an esophagus.
Figure 3B:
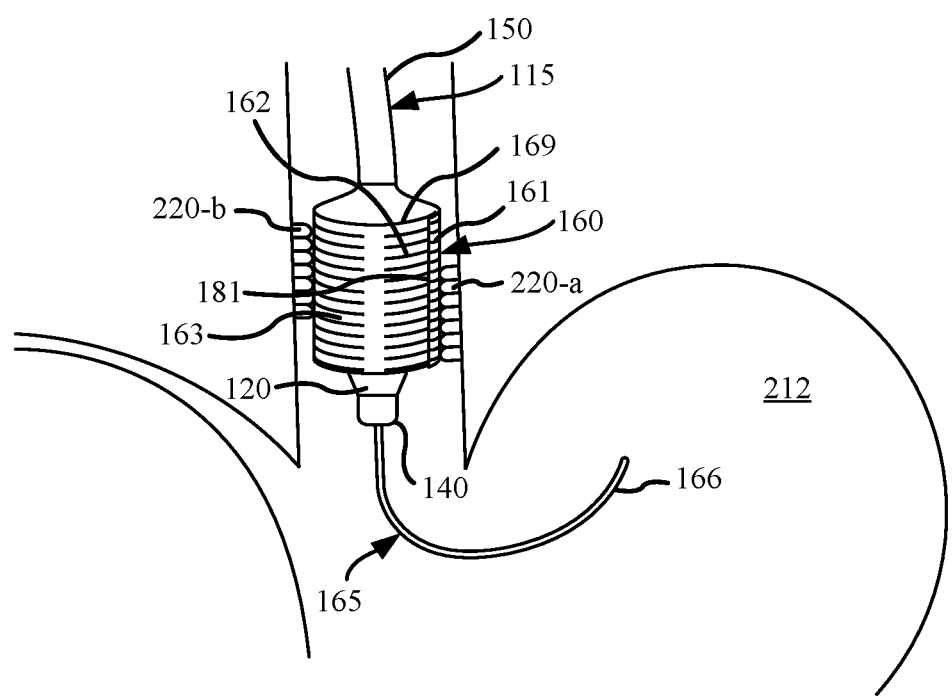
FIG. 3B is a schematic view of an ablation device, in an unfurled/expanded mode, within an esophagus

Referring now to FIG. 3A and FIG. 3B, the expansion member 120 may be inserted into the body in any of various ways including, for example, guide assembly 165 placement, endoscopic placement, surgery, or by other means. Expansion member 120 may be an example of expansion member 120 of FIG. 1A and/or FIG. 1B. Referring now to FIG. 3A, the expansion member 120 is shown in a collapsed configuration in accordance with various embodiments. The expansion member 120 may be configured for transitioning between the collapsed configuration shown and an expanded configuration as shown in FIG. 3B. In the expanded configuration, at least one dimension of the expansion member 120 may have increased. In various embodiments, the expanded configuration is significantly larger than the collapsed configuration and allows the ablation structure 160 to contact a treatment surface such as columnar epithelial cells 220-*a* and/or 220-*b*. The ablation structure 160 may be delivered to the treatment site within the body lumen while in a collapsed state. This low-profile configuration may allow for ease-of-access to the treatment site without discomfort or complications to the patient. When an endoscope (not shown) is used, the portion 150 of catheter 115 may be positioned along the outside of the endoscope. Alternately, an endoscope may be used to visualize the pathway that expansion member 120 should follow during placement. The distal end 166 of the guide assembly 165 may be positioned along the outside of an endoscope and left in the body lumen after removal of the endoscope. The proximal end 167 (see e.g., FIG. 1B) of the guide assembly 165 may be inserted into the distal end 140 of the catheter 115 and the catheter 115 inserted into the esophagus following the path determined by the guide assembly 165.

An ablation structure 160 may be provided and may be coupled to the expansion member 120 and positioned near portion 150 of catheter 115. In some instances, the expansion member 120 is bonded to the portion 150 of catheter 115. The ablation structure 160 may include one or more electrodes 169. The one or more electrodes 169 may be arranged into multiple longitudinal electrodes zones 161, 162 of equal or varying widths. The one or more electrodes 169 may be coupled to a power source 105 (see e.g., FIG. 1A) configured for powering the one or more electrodes and/or longitudinal electrode zones 161, 162 at levels appropriate to provide the ablation of tissue to a predetermined depth of tissue.

In some embodiments, the ablation structure 160 includes a flexible, non-distensible backing. For example, the ablation structure 160 may include a thin, rectangular sheet of polymer materials such as polyimide, polyester or other flexible thermoplastic or thermosetting polymer film. The ablation structure 160 may also include polymer covered materials, or other nonconductive materials. Additionally, the backing may include an electrically insulating polymer, with an electro-conductive material, such as copper, deposited onto a surface so that an electrode pattern may be etched into the material to create an electrode array.

The ablation structure 160 may be operated in direct contact with the wall of the tissue site. This may be achieved by coupling the ablation structure 160 to an expansion member 120, which has a configuration that may be expandable in a shape that conforms to the dimensions of the inner lumen of the treatment site, such as the human lower esophageal tract. The ablation structure 160 may be positioned so that energy may be uniformly applied to the inner circumference of the lumen where treatment is desired. This may be accomplished by first positioning the expansion member 120 at the treatment site in a collapsed configuration with the ablation structure 160 furled around the expansion member 120. Once the apparatus is advanced to the appropriate site, the expansion member 120 may be expanded, transitioning the ablation structure 160 from a furled state to an unfurled state, thus engaging the internal wall of the lumen.

With reference to FIG. 3B, the ablation structure 160 uniformly engages the inner wall of the lumen with one or more electrode zones 161, 162 having a constant density so that the energy may be uniformly applied to all or a portion of the circumference of the inner lumen of the esophagus or other tissue site. An expansion member 120 may include, for example, a balloon, such as a compliant balloon and/or a balloon with a tapered geometry that expands to an expanded configuration when inflated.

In some embodiments, as the expansion member 120 expands and the ablation structure 160 unfurls, additional electrodes or electrode zones 163 are exposed from beneath an overlapping portion 181 of the ablation structure 160. Selective enabling of one or more longitudinal electrodes 169 and/or longitudinal electrode zones 161, 163 allows the total surface area of the ablation structure 160 to be divided, thus accommodating certain power limitations of a power source, and thereby providing appropriate energy density to the tissue. The ablation structure 160 may extend an arc length distance greater than the circumference of the expansion member 120 such that when the expansion member 120 expands, gapless circumferential ablation is affected for various sized body lumens.

The ablation structure 160 may be positioned and energy applied to the inner circumference of a body lumen treatment site. This may be accomplished by first positioning the expansion member 120 to the treatment site in a collapsed configuration. Once the ablation structure 160 is advanced to the appropriate treatment site, expansion member 120 may be expanded, advancing the ablation structure 160 to engage the internal wall of the body lumen. The desired treatment energy may then be delivered to the tissue by selectively enabling one or more longitudinal electrodes and/or longitudinal electrode zones 161, 162, 163. In some instances, all longitudinal electrodes and/or longitudinal electrode zones 161, 162, 163 are sequentially enabled starting with the longitudinal electrode and/or longitudinal electrode zone 161 adjacent the free or overlapping edge 181 of ablation structure 160. The detection of a fully-shielded longitudinal electrode and/or longitudinal electrode zone may stop energy delivery to additional longitudinal electrodes and/or longitudinal electrode zones in the sequence as the additional longitudinal electrodes and/or longitudinal electrode zones are not in contact with the tissue of the body lumen.

In certain embodiments, the ablation structure 160 delivers a variety of different types of energy including but not limited to, radio frequency, microwave, ultrasonic, resistive heating, chemical, a heatable fluid, optical including without limitation, ultraviolet, visible, infrared, collimated or non-collimated, coherent or incoherent, or other light energy, and the like.

Referring now to FIG. 4, the distal portion of a general system 400 for delivering treatment to a target treatment area is shown in a collapsed configuration in accordance with various embodiments. System 400 may be an example of system 100 or 100-a described with reference to FIG. 1A or 1B and may include a catheter 115, an expansion member 120 coupled with the catheter 115, and an ablation structure 160 furled around the expansion member 120. To engage the inner surface of a body lumen that is larger than the collapsed diameter of the expansion member 120, expansion member 120 may be expanded (see e.g., FIG. 5) until the desired pressure is exerted on the inside wall of the lumen. The expansion member 120 may be expanded such that pressure applied to the body lumen is less than a pressure that would otherwise result in damage such as, for example, by lacerating or perforating the lumen. Although the exposed surface area of the ablation structure 160 increases as the expansion member 120 expands, the individually and sequentially enabled electrodes or electrode zones may maintain a constant electrode density across the surface of ablation structure 160. Energy, including but not limited to an RF signal, delivered to the electrodes or electrode zones may provide a uniform treatment within each region to a precise depth of tissue. After the treatment has been administered, the expansion member 120 may be collapsed and the system removed from the body lumen.

In some embodiments, the ablation structure 160 includes a large single electrode divided into adjacent longitudinal electrode zones 161, 162 of either uniform or varying widths, configured to reduce the degree of ablation-region overlap and thus reduce the degree of over ablation. Longitudinal electrode zones 161, 162 may be selectively enabled via multiple transmission lines 170 extending between the power source 105 (see e.g., FIG. 1A) and the longitudinal electrode zones 161, 162. The ablation structure 160 may include an electrode array 163 etched on its surface and may be aligned between the distal end 404 and proximal end 402 of the expansion member 120.

Referring now to FIG. 5, the system 400 described with reference to FIG. 4 is shown in an expanded configuration in accordance with various embodiments. When the expansion member 120 is inflated or otherwise expanded, ablation structure 160 unfurls, exposing electrodes 504, 506. The longitudinal electrodes 502, 504, 506 of ablation structure 160 may be selectively enabled via multiple transmission lines 170 extending between the power source 105 (see e.g., FIG. 1A) and the longitudinal electrodes 502, 504, 506. For example, isolated transmission wires 170-a, 170-b, 170-c may be individually wired to electrodes or electrode zones 502, 504, 506. The wires may be individually insulated with heat shrink tubing along the entire length of the catheter 115. Each of the wires may terminate to a mini connector plug of the power source 105 or a switching printed circuit board controller configured to drive transmission channels in addition to the channels of the power source 105. Under this configuration, power may be delivered to one or more electrodes or electrode zones selectively such that treatment may be administered to a specific area along the ablation structure 160. The switching printed circuit board may be included on the catheter 115, external to the power source 105, or within the power source 105.

In some embodiments, the ablation structure 160 is configured such that one or more of the longitudinal electrodes or longitudinal electrode segments positioned at the free end 181 of the ablation structure 160 have a width greater than the width of the remaining longitudinal electrodes or longitudinal electrode segments nearer the bonded end (not shown) of the ablation structure 160. When a minimum lumen size may be anticipated, for example, about 16 mm in the case of an esophagus, the arc length corresponding to the circumference of this minimum size may be used as the width for one or more wider longitudinal electrodes or longitudinal electrode regions positioned adjacent to the free end 181 of the ablation structure 160. For example, if the maximum lumen size may be 37 mm, the total arc length of the one or more electrodes may be calculated as 37*pi=116 mm. In the case of a single electrode with multiple longitudinal electrode zones, the electrode area equal to the arc length of the minimum lumen size (16*pi=50 mm) may be configured as two electrode regions with a width of 25 mm each. The remaining regions may include a set of narrow width electrode zones, for example, seven electrode zones of 10 mm each. This may result in a reduced number of total regions as compared to using a set of fixed width regions, while continuing to provide narrow width regions for potential areas of ablation structure overlap.

Figure 6:
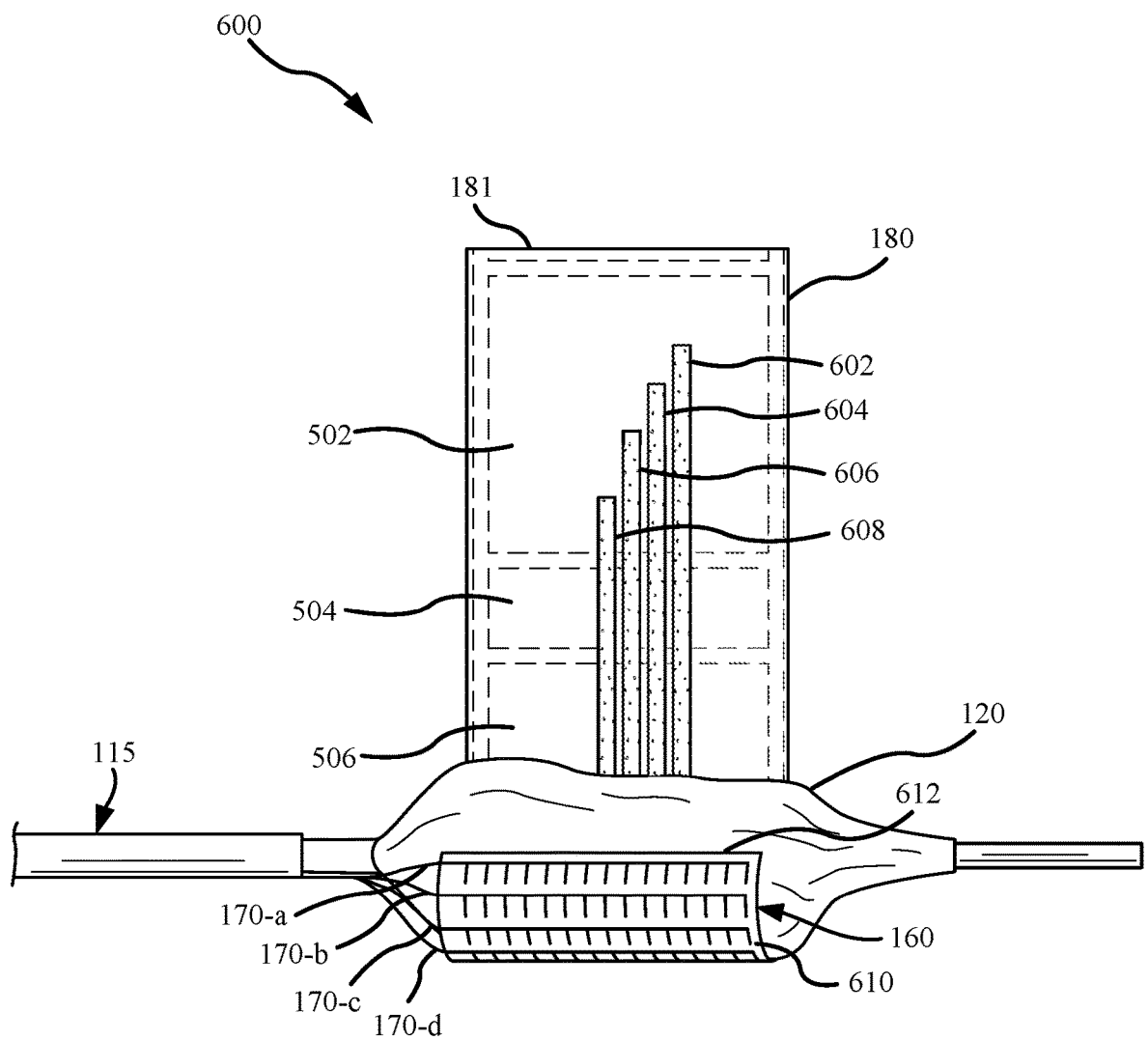
FIG. 6 is a perspective view of the partially unfurled ablation device of FIGS. 3-5.

With reference now to FIG. 6, the distal portion of a general system 600 for delivering treatment to a target treatment area is shown in a collapsed configuration in accordance with various embodiments. System 600 may be an example of systems 100, 100-a, or 400 described with reference to FIG. 1A, 1B, 4, or 5, and may include a catheter 115, an expansion member 120 coupled with the catheter 115, and an ablation structure 160. The ablation structure 160 is shown in a partially unfurled configuration to illustrate the underside of ablation structure 160. The ablation structure 160 may be coupled with an ablation structure support 180 that is bonded or otherwise attached to the expansion member 120. For example, a first end 612 of the ablation structure 160 may be bonded or otherwise attached to the expansion member 120. An adhesive bond may be implemented along the full length or partial length of the contact zone between the first end 612 of the ablation structure 160 and the expansion member 120. In certain instances, adhesion occurs when the expansion member 120 is in an expanded configuration. The internal surface of the ablation structure 160 may include four variable-width springs 602, 604, 606, 608 that extend perpendicularly from the bonded first edge 612 of the ablation structure 160 and perpendicular to the longitudinal axis of the expansion member 120, configured such that localized spring density increases linearly toward the free end 181 of the ablation structure 160. The ablation structure 160 may include a single electrode segregated into longitudinal segments 502, 504, 506, 610 of one or more varying widths. The longitudinal electrode segment 502 adjacent to the free edge 181 of the ablation structure 160 may have a width greater than the width of the other longitudinal electrode segments 504, 506, 610. Each longitudinal electrode segment 502, 504, 506, 610 may be coupled to a power source 105 (see e.g., FIG. 1A) by a wiring structure isolated from the wiring structure for the other longitudinal electrode segments 170-a, 170-b, 170-c, 170-d.

Figure 7:
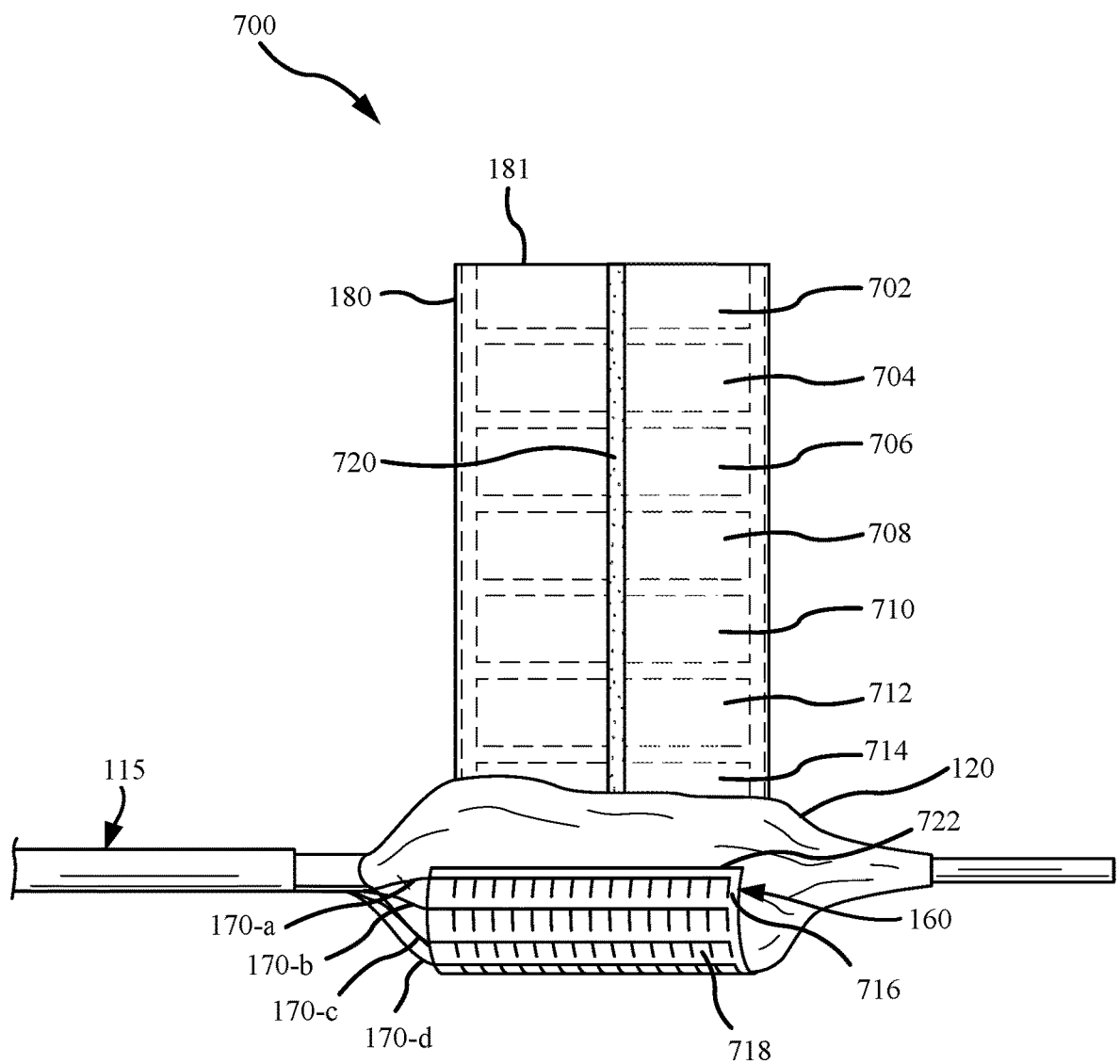
FIG. 7 is a perspective view of the partially unfurled distal portion of the ablation device of FIGS. 3-5 with a single spring and multiple longitudinal electrode regions of uniform widths.

In some embodiments, an ablation structure 160 includes a large single electrode divided into adjacent longitudinal electrode zones of uniform width configured to reduce the degree of ablation-region overlap and thus reduce the degree of over ablation. Such a uniform width configuration may be useful when a minimum size lumen is not known, such as when the ablation system is used for a variety of different body lumens. With reference now to FIG. 7, the distal portion of a general system 700 for delivering treatment to a target treatment area is shown in a collapsed configuration in accordance with various embodiments. System 700 may be an example of systems 100, 100-a, 400, or 600 described with reference to FIG. 1A, 1B, or 4-6, and may include a catheter 115, an expansion member 120 coupled with the catheter 115, and an ablation structure 160. The ablation structure 160 is shown in a partially unfurled configuration to illustrate the underside of ablation structure 160. The ablation structure 160 may be coupled with an ablation structure support 180 that is bonded or otherwise attached to the expansion member 120 along bonded edge 722. The underside surface of the ablation structure 160 may include a single spring 720 extending from the bonded edge 722 of the ablation structure 160 perpendicular to the longitudinal axis of the expansion member 120. A single electrode may be segregated into longitudinal zones 702, 704, 706, 708, 710, 712, 714, 716, 718 of uniform widths. Each longitudinal electrode zone 702, 704, 706, 708, 710, 712, 714, 716, 718 may be coupled to a power source 105 (see e.g., FIG. 1A) by a wiring structure isolated from the wiring structure for the other longitudinal electrode segments 170-a, 170-b, 170-c, 170-d (additional isolated wiring structures not shown).

Figure 8:
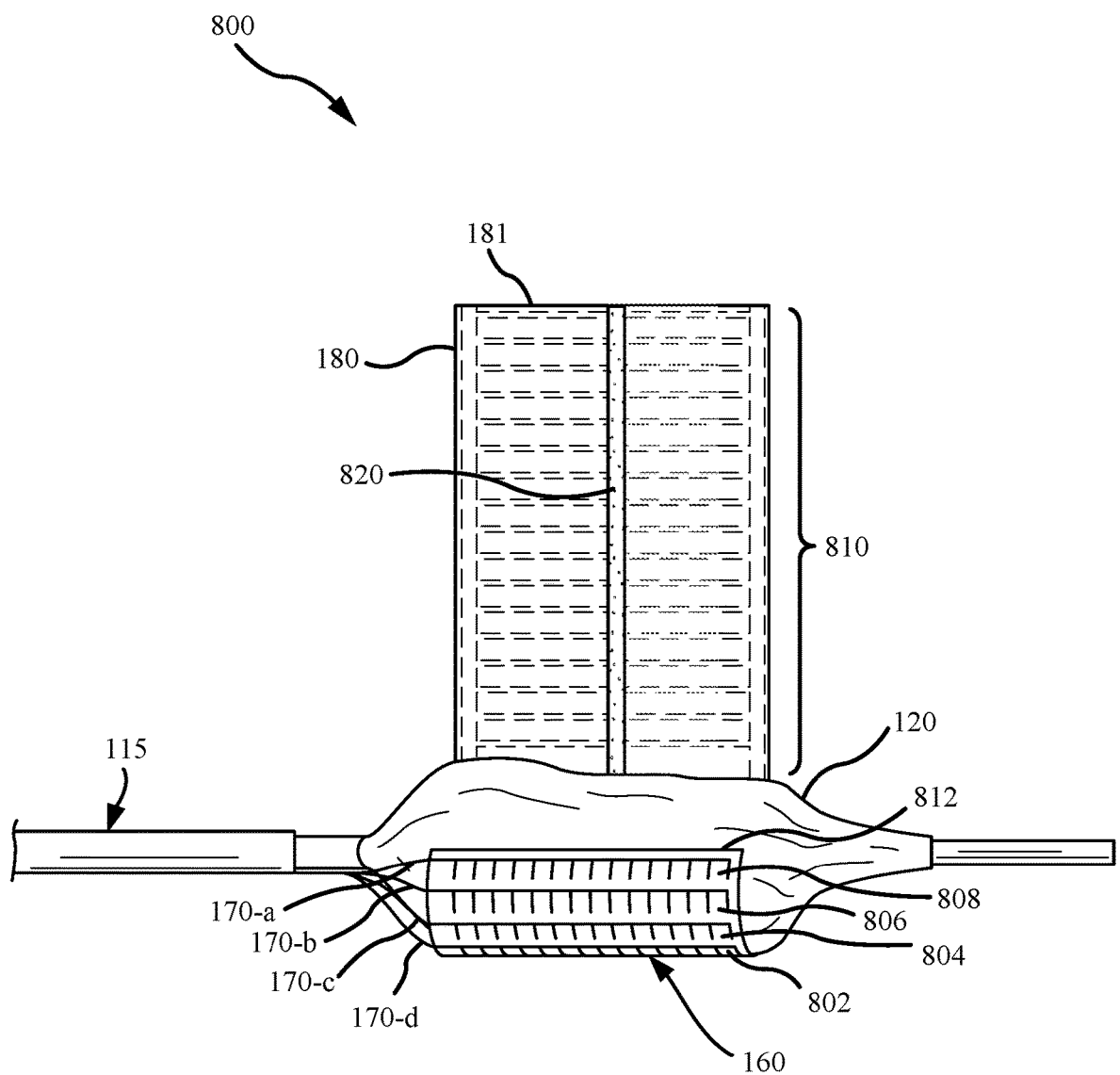
FIG. 8 is a perspective view of the partially unfurled distal portion of the ablation device of FIGS. 3-5 with a single spring and multiple longitudinal electrode regions of uniform narrow widths.

In some embodiments, an ablation structure 160 includes a large single electrode segregated into adjacent longitudinal electrode zones of uniform narrow width, for example, with width less than 10 mm, configured to reduce the degree of ablation-region overlap and thus reduce the degree of over ablation in those regions where overlap is present. With reference now to FIG. 8, the distal portion of a general system 800 for delivering treatment to a target treatment area is shown in a collapsed configuration in accordance with various embodiments. System 800 may be an example of systems 100, 100-a, 400, 600, or 700 described with reference to FIG. 1A, 1B, or 4-7, and may include a catheter 115, an expansion member 120 coupled with the catheter 115, and an ablation structure 160. The ablation structure 160 is shown in a partially unfurled configuration to illustrate the underside of ablation structure 160. The ablation structure 160 may be coupled with an ablation structure support 180 that is bonded or otherwise attached to the expansion member 120 along bonded edge 812. The underside surface of the ablation structure 160 may include a single spring 820 extending from the bonded edge 812 of the ablation structure 160 perpendicular to the longitudinal axis of the expansion member 120. A single electrode may be segregated into longitudinal zones 802, 804, 806, 808, 810 of uniform widths. Each longitudinal electrode zone 802, 804, 806, 808, 810 may be coupled to a power source 105 (see e.g., FIG. 1A) by a wiring structure isolated from the wiring structure for other longitudinal electrode zones 170-a, 170-b, 170-c, 170-d (additional isolated wiring structures not shown).

Figure 9:
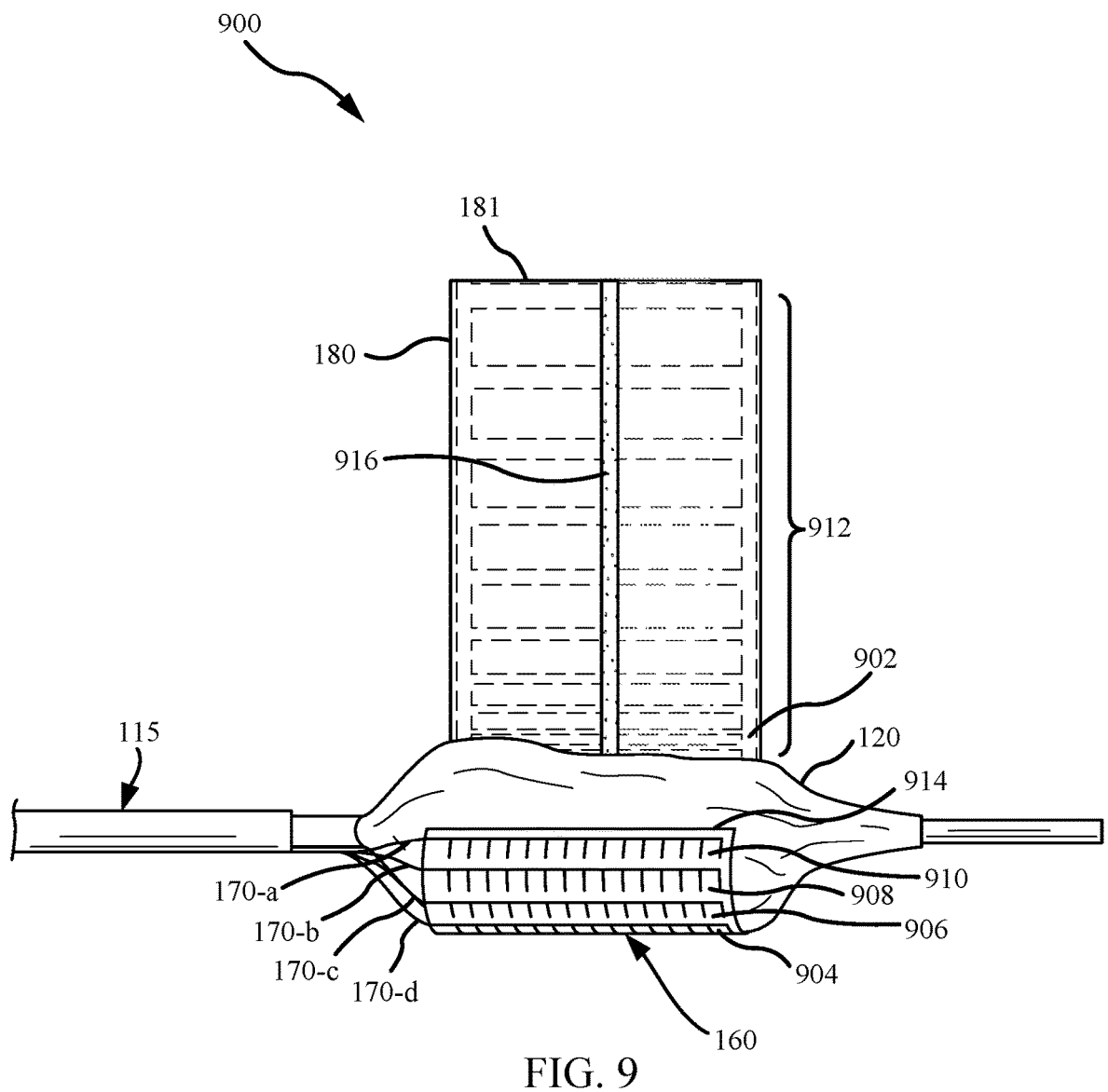
FIG. 9 is a perspective view of the partially unfurled distal portion of the ablation device of FIGS. 3-5 with a single spring and multiple variable-length longitudinal electrode regions of successively decreasing widths.

In some embodiments, an ablation structure 160 includes a large single electrode segregated into adjacent longitudinal electrode zones of varying widths configured to reduce the degree of ablation-region overlap and thus reduce the degree of over ablation. With reference now to FIG. 9, the distal portion of a general system 900 for delivering treatment to a target treatment area is shown in a collapsed configuration in accordance with various embodiments. System 900 may be an example of systems 100, 100-a, 400, 600, 700, or 800 described with reference to FIG. 1A, 1B, or 4-8, and may include a catheter 115, an expansion member 120 coupled with the catheter 115, and an ablation structure 160. The ablation structure 160 is shown in a partially unfurled configuration to illustrate the underside of ablation structure 160. The ablation structure 160 may be coupled with an ablation structure support 180 that is bonded or otherwise attached to the expansion member 120 along bonded edge 914. The underside surface of the ablation structure 160 may include one spring 916 extending from the bonded edge 914 of the ablation structure 160 perpendicular to the longitudinal axis of the expansion member 120. A single electrode may be segregated into longitudinal zones 902, 904, 906, 908, 910, 912 of varying widths. The adjacent longitudinal electrode zones 912 extending from the free edge 181 of the ablation structure 160 decrease in width linearly until reaching a minimum width such as, for example, 10 mm. All subsequent adjacent longitudinal electrode zones 902, 904, 906, 908, 910 may have a width equal to the minimum width. Each longitudinal electrode segment 902, 904, 906, 908, 910, 912 may be coupled to a power source 105 (see e.g., FIG. 1A) by a wiring structure isolated from the wiring structure for other longitudinal electrode zones 170-a, 170-b, 170-c, 170-d (additional isolated wiring structures not shown).

Figure 10A:
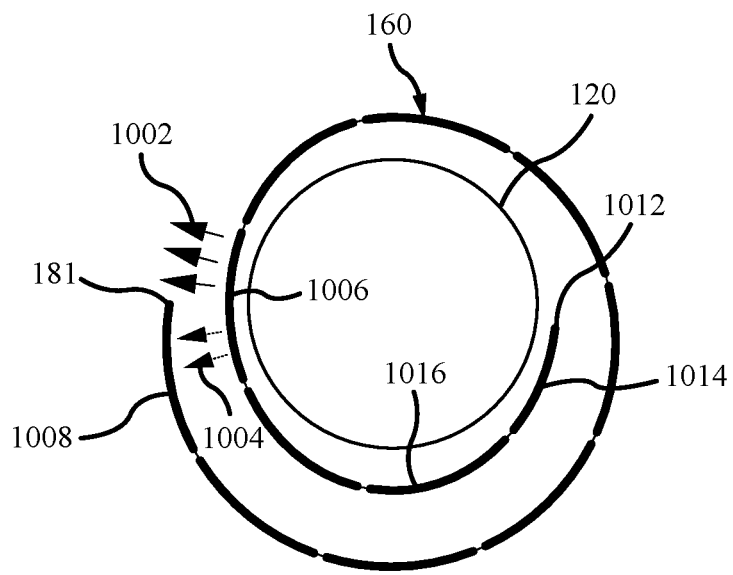
FIG. 10A is a top cross-sectional view of an ablation structure of the ablation device of FIGS. 3-5 in an unfurled/expanded mode with a partially overlapped electrode region and fully overlapped electrode regions.
Figure 10B:
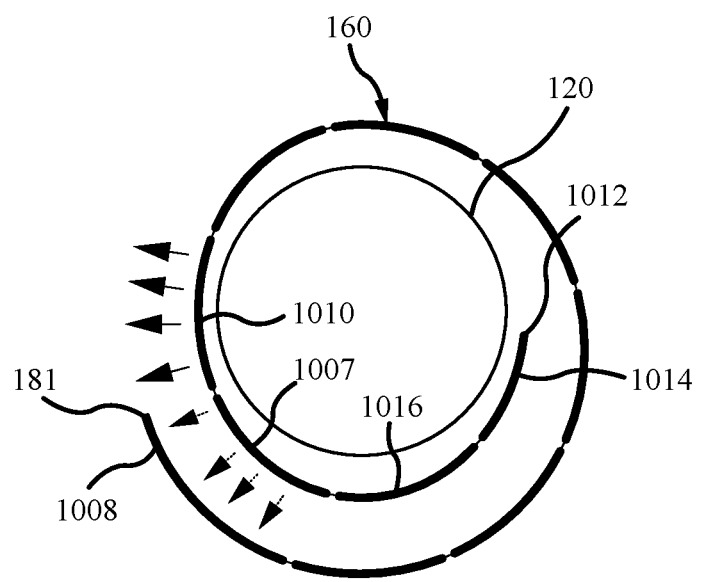
FIG. 10B is a top cross-sectional view of an ablation structure of the ablation device of FIGS. 3-5 in an unfurled/expanded mode with fully overlapped electrode regions.

Referring now to FIG. 10A and FIG. 10B, a cross sectional view of an ablation structure 160 and expansion member 120 is shown in accordance with various embodiments. The ablation structure 160 may be an example of the ablation structure 160 described in connection with FIGS. 1A, 1B, 4 and/or 5. As shown, the ablation structure 160 may be attached at a first end 1012 to the expansion member 120 (adhesion not shown). The free end 181 of the ablation structure 160 may be furled around the expansion member 120, overlapping the bonded end 1012 one or more times. As the expansion member 120 expands, the ablation structure 160 unfurls and further exposes additional electrodes or electrode zones that had previously been shielded by the overlapping portion 181 of the ablation structure 160.

At any given inflation diameter, one or more electrodes or electrode zones may be in contact with a region of the treatment tissue and one or more electrode segments may be in contact with the insular backing of the ablation structure 160 or ablation structure support 180. Electrode traces may be bridged with conductive material, such as, for example, saline, mucous, or tissue coagulum. In the absence of mitigating structures or procedures, these materials may come in contact with the insular backing of the ablation structure 160. This can drain the energy intended for tissue treatment both where a single electrode is used and/or where ablation zones are oriented circumferentially, thus reducing the intended energy delivery and thereby reducing the density/tissue ablation depth below a threshold level. In some embodiments, each longitudinal electrode or longitudinal electrode zone is separately controlled, separately wired, or both such that each longitudinal electrode or longitudinal electrode zone may be unaffected by the presence or absence of electrode regions covered by the ablation structure and/or coated by conductive matter such as fluids or tissue. The total energy delivered to each longitudinal electrodes or longitudinal electrode zone may be calculated based on the longitudinal electrode's or longitudinal electrode zone's total active surface area according to ablation parameters developed in the art such as, for example, the parameters used with ablation catheter systems.

Often the free end 181 of the ablation structure 160 fully or partially overlaps one or more longitudinal electrode regions. When an electrode segment 1006 is only partially exposed (i.e., partially covered up with an overlapping portion 181 of the ablation structure 160), as shown in FIG. 10A, and therefore only in partial contact with a tissue treatment area, energy 1002 may be delivered to the treatment area and energy 1004 may be delivered to the backing of the ablation structure 160, which may result in an energy delivery profile that deviates from an intended energy delivery profile, delivering an excessive amount of energy to the treatment tissue region. Configuring the longitudinal electrodes or longitudinal electrode segments such that the width of the inner-most partially exposed longitudinal electrode or longitudinal electrode zone does not exceed a predetermined percentage of the circumference of the treatment area, such as, for example, about twenty percent, may reduce this effect.

Various methods may be used to limit the extent to which energy may be over-delivered to tissue treatment areas in contact with partially shielded longitudinal electrodes or longitudinal electrode zones, such as electrode zone 1006 of FIG. 10A. A channel regulation module (see e.g., FIG. 1C) may include computer instructions configured to enable each adjacent longitudinal electrode or longitudinal electrode zone sequentially starting with the longitudinal electrode or longitudinal electrode zone 1008 adjacent to the free edge 181 of the ablation structure 160. Computer instructions may be further provided to execute impedance measurements and calculations such that the degree of ablation may be controlled in real time. A partially shielded longitudinal electrode or longitudinal electrode zone 1006 may often have higher impedance than unshielded longitudinal electrodes or longitudinal electrode zones such as zone 1010 shown in FIG. 10B. The impedance of each longitudinal electrode or longitudinal electrode zone may be compared to the impedance measurements obtained for previous zones in advance of enabling each longitudinal electrode or longitudinal electrode zone. Detection of higher impedance may be indicative of a partially occluded (e.g., 1006 of FIG. 10A) or a fully occluded (e.g., 1007 of FIG. 10B) electrode or electrode zone. Computer instructions may be further provided to reduce ablation time and/or lower voltage delivered to the partially/fully occluded electrode or electrode zone 1006, 1007 as determined by the detection of higher starting impedance. Computer instructions may be further provided that cease sequential enablement of electrodes or electrode zones 1014, 1016 subsequent to the detection of a first partially or fully occluded electrode or electrode zone 1006, 1007. In addition to having starting impedance greater than the impedance of unshielded longitudinal electrodes or longitudinal electrode zones 1010, occluded electrodes or electrode zones 1006, 1007, may often experience an increased rate of change in impedance as compared to unshielded longitudinal electrodes or longitudinal electrode zones 1010. Computer instructions may be provided that compare the impedance change rate during ablation with the impedance change rate from prior ablations in the same patient or previous patients, where detection of a higher rate of impedance change indicates the currently enabled electrode or electrode zone may be partially shielded. Computer instructions may be further provided to reduce ablation time and/or lower the voltage delivered to the occluded electrode or electrode zone.

Figure 11A:
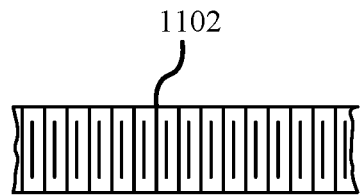
FIG. 11A is a schematic view of an electrode zone array pattern of the ablation device of FIGS. 3-5.
Figure 11B:
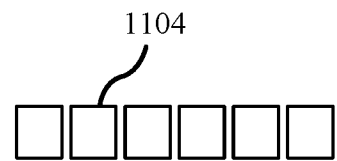
FIG. 11B is a schematic view of an electrode zone array pattern of the ablation device of FIGS. 3-5.
Figure 11C:
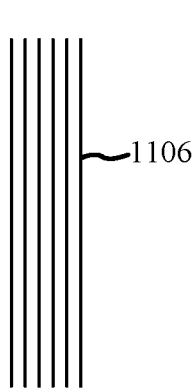
FIG. 11C is a schematic view of an electrode zone array pattern of the ablation device of FIGS. 3-5.
Figure 12A:
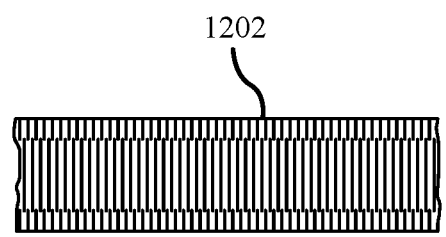
FIG. 12A is a schematic view of the electrode patterns of the ablation device of FIGS. 3-5.
Figure 12B:
FIG. 12B is a schematic view of an electrode zone array pattern of the ablation device of FIGS. 3-5.
Figure 12C:
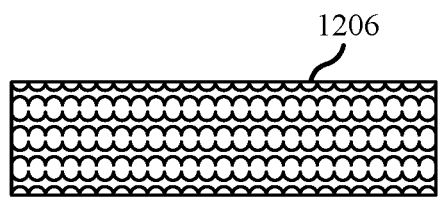
FIG. 12C is a schematic view of an electrode zone array pattern of the ablation device of FIGS. 3-5.
Figure 12D:
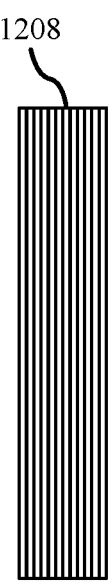
FIG. 12D is a schematic view of an electrode zone array pattern of the ablation device of FIGS. 3-5.

Referring now to FIG. 11A through FIG. 11C, the electrode patterns may be varied depending on the length of the site to be treated, the depth of the mucosa and submucosa, in the case of the esophagus, at the site of treatment, and other factors. The electrode patterns 1102-1208, may be examples of electrode patterns included with the electrode array 163 of FIG. 4 and FIG. 5. An electrode array pattern may be composed of particular electrode elements that may be arranged in various configuration, such as, for example, a circumferential orientation or a longitudinal orientation. An electrode element is a conductive element of an electrode array. In some instances, electrode elements are aligned parallel to one another. The density of the electrode elements may affect the depth of an ablation treatment. The longitudinal electrode or longitudinal electrode zone patterns may be aligned in an axial or transverse direction across the one or more electrodes or formed in a linear or non-linear parallel matrix or series of bipolar pairs or monopolar electrodes. One or more different patterns may be coupled to various locations of the ablation structure 160. For example, an electrode array, as shown in FIG. 11A through FIG. 11C, may comprise a pattern of bipolar axial interlaced finger electrodes 1102, monopolar rectangles 1104 with 1 mm separation, or six bipolar rings 1106 with 2 mm separation. Other suitable RF electrode patterns may be used including, without limitation, those patterns shown in FIG. 12A through FIG. 12D. Patterns may include, for example, bipolar axial interlaced finger electrodes 1202 with 0.3 mm separation, monopolar bands 1204 with 0.3 mm separation, bipolar rings 1208 with 0.3 mm separation, and/or undulating electrodes 1206 with 0.2548 mm separation.

The depth of treatment may be controlled by the selection of appropriate treatment parameters by the operator as described in the examples set forth herein. One parameter that may affect the depth of treatment is the density of electrode elements. As the spacing between electrode elements decreases, the depth of treatment of the affected tissue also decreases when RF energy is delivered in bipolar fashion across the electrodes. Very close spacing of the electrode elements may limit the current and resulting ohmic heating to a shallow depth such that injury and heating of the submucosal layer are minimized. For treatment of esophageal tissue using RF energy, it may be desirable to have a spacing between adjacent electrode elements be no more than, (i) 3 mm, (ii) 2 mm, (iii) 1 mm (iv) 0.5 mm or (v) 0.3 mm (vi) 0.1 mm and the like.

In various embodiments, the dimensions of the electrodes and spacing between the electrode elements are selected to enable controlled depth ablation. Examples of electrode configurations for controlled depth ablation are described in U.S. Pat. No. 6,551,310 Ganz et al.), U.S. Pat. No. 7,150,745 (Stern et al.), U.S. Pat. No. 7,344,535 (Stern et al.), U.S. Pat. No. 7,530,979 (Ganz et al.), U.S. Pat. No. 7,993,336 (Jackson et al.), U.S. Pat. No. 8,012,149 (Jackson et al.), U.S. Pat. No. 8,192,426 (Stern et al.), U.S. Pat. No. 8,439,908 (Utley et al.), and U.S. Pat. No. 8,398,631 (Ganz et al.), the entire contents of each which are incorporated herein for all purposes. In various embodiments, the power generator and/or a channel regulation module (see e.g., FIG. 1C) are configured to control the application of energy using the ablation structure 160 to effect ablation of tissue to a controlled depth.

Although described in terms of an electrode array for RF ablation, those skilled in the art will appreciate that the ablation structure suitable for use with the embodiments described herein may be configured for administering other forms of therapy or diagnosis. For example, the techniques described above may be applied to form an antenna for microwave ablation. In another example, the operative member may include sensor elements overlaying the expandable support device. Monopolar RF configurations may also be used in some embodiments. Some embodiments may utilize bipolar RF configurations.

In various embodiments, the ablation structures described herein are ablation devices, and in some embodiments, RF ablation devices. In various embodiments, the ablation structures described herein are configured for thermal ablation. In some embodiments, the ablation structures described herein are configured to heat surrounding tissue by resistive heating or conduction. Embodiments of ablation structures described herein may be configured to treat or diagnose the surrounding tissue by other modalities.

In various embodiments, the ablation structures described herein are configured for ablation of abnormal tissue in the esophagus. In some instances, the ablation structures described herein are configured for ablation of abnormal tissue in the lower esophageal sphincter. In certain implementations, the ablation structures described herein are configured for ablation of Barrett's esophagus and/or precancerous tissue in the epithelium without injuring the underlying muscularis. In some embodiments, the ablation structures described herein are configured for use in a variety of body lumens and organs including, but not limited to, the gastrointestinal (GI) tract (e.g. the esophagus or duodenum), the alimentary tract, the digestive system (e.g. the bile duct), the cardiovascular system, the endocrine system (e.g. the pancreas), and the respiratory system.

In various embodiments, the ablation structures described herein are configured to ablate tissue to a predetermined depth. In some cases, the ablation structures described herein are configured to ablate mucosal tissue without injuring the underlying submucosal tissue. In certain instances, the ablation structures described herein are configured to ablate mucosal tissue without injuring the underlying muscularis. In some implementations, the ablation structures described herein are configured to apply the appropriate level of energy to the tissue to achieve an ablation depth that does not extend beyond the submucosa layer of the esophagus. In some embodiments, the ablation structures described herein are configured to control the depth of ablation to the epithelium. In some instances, the ablation structures described herein are configured for superficial ablation. For example, various embodiments of an ablation structure may be configured to sear the tissue surface. In certain cases, the ablation structures described herein are configured to deliver sufficient energy to initiate regrowth of tissue, for example, in a mucosal layer.

Controlling the depth of ablation may be based on several factors such as power and treatment time. In various embodiments, the power source activates the longitudinal electrodes or longitudinal electrode zones with sufficient power and for a sufficient amount of time to ablate tissue to a predetermined depth. In an exemplary embodiment, the power source activates one or more longitudinal electrodes or longitudinal electrode zones with sufficient power and for a length of time necessary to deliver between about 1 J/sq.-cm and about 50 J/sq.-cm, between about 10 J/sq.-cm and about 40 J/sq.-cm, between about 15 J/sq.-cm and about 105 J/sq.-cm, between about 25 J/sq.-cm and about 105 J/sq.-cm, between about 30 J/sq.-cm and about 105 J/sq.-cm, between about 35 J/sq.-cm and about 105 J/sq.-cm, or between about 40 J/sq.-cm and about 105 J/sq.-cm. Other energy per unit area amounts may be utilized in some embodiments.

In various embodiments, the power source 105-*a* (see e.g., FIG. 1B) may be configured to deliver between about 10 Watts/sq.-cm and about 50 Watts/sq.-cm, between about 10 Watts/sq.-cm and about 40 Watts/sq.-cm, between about 10 Watts/sq.-cm and about 30 Watts/sq.-cm, between about 15 Watts/sq.-cm and about 30 Watts/sq.-cm, or between about 15 Watts/sq.-cm and about 40 Watts/sq.-cm. Other energy per unit area amounts may be utilized in some embodiments.

In some instances, the power source 105-*a* is configured to activate the longitudinal electrodes or longitudinal electrode zones for between about 10 ms and about 5 minutes, between about 100 ms and about 1 minute, between about 100 ms and about 30 seconds, between about 10 ms and about 1 second, between about 100 ms and about 1 second, or between about 300 ms and about 800 ms. In certain embodiments, the power generator is configured to activate the electrodes for less than 1 second, less than 500 ms, or less than 300 ms. In some implementations, the power source is configured to deliver about 40 W/sq.-cm for a duration of about 300 ms to about 800 ms. In some embodiments, the power source is configured to deliver between about 12 J/sq.-cm to about 15 J/sq.-cm for a duration of about 300 ms to about 800 ms. Other energy per unit area amounts and time amounts may be utilized in some embodiments.

Figure 13:
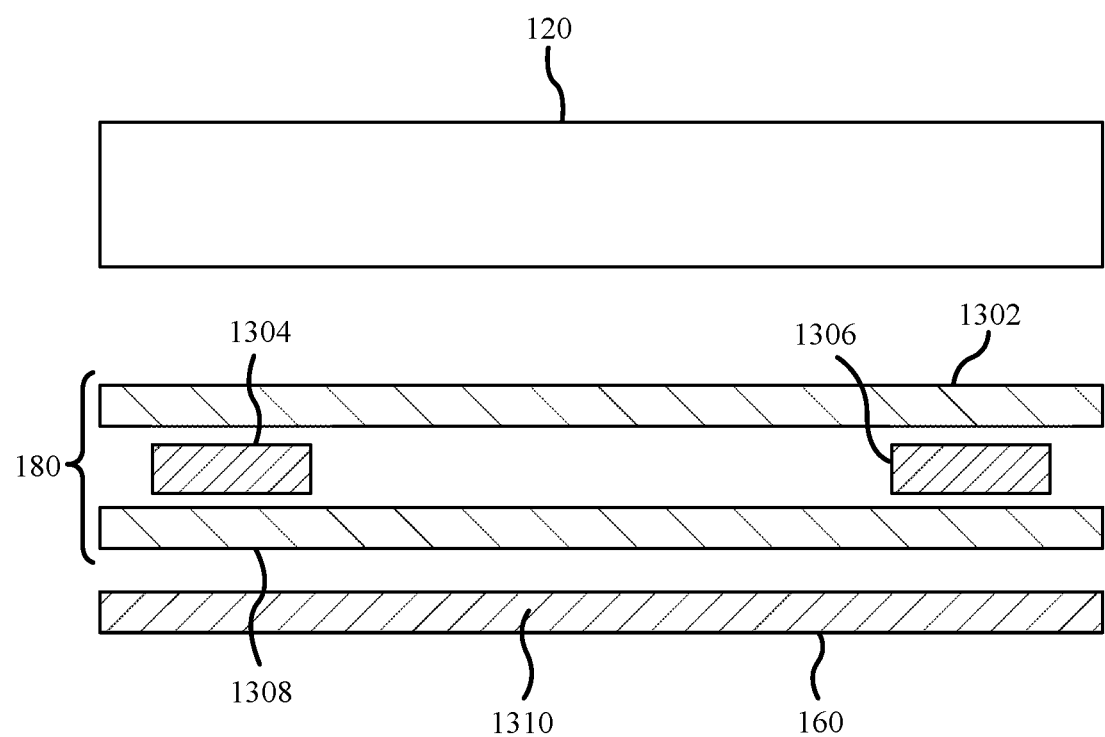
FIG. 13 is a cross section view of an ablation structure of the ablation device of FIGS. 3-5.

In certain cases, the ablation structure support 180 is spirally furled about a longitudinal axis of the expansion member 120. The electrode pattern may be aligned in axial or traverse direction across the backing, formed in a linear or non-linear parallel array or series of bipolar pairs, or other suitable pattern. Referring now to FIG. 13, a cross sectional view of an expansion member 120, an ablation structure support 180, and an ablation structure 160 is shown in accordance with various embodiments. In some embodiments, the ablation structure support 180 includes a flexible, non-distensible backing. For example, the backing may include a thin, rectangular sheet of a polymer material such as polyimide, polyester or other flexible thermoplastic or thermosetting polymer film, polymer covered materials, or other nonconductive materials. The backing may also include an electrically insulating polymer, with an electroconductive material, such as copper, deposited onto a surface. The ablation structure 160 may be formed from a metallic layer 1310 that may be etched to include a pattern of electrodes using any known technique, such as etching using masks.

One or more constant force springs 1304, 1306 may be attached to a flexible backing 1302 by application of an adhesive substance 1308. A polytetrafluoroethylene film may be etched on one side and adhered to the spring side of the ablation structure 160. The entire ablation structure 160 may be laminated as a flat sheet, providing for friction reduction during the transition between furled configurations and unfurled configurations, thus reducing the pressure required to transition to an unfurled configuration. Other methods of constructing an ablation structure 160 and ablation structure support 180 may also be utilized. In some instances, the ablation structure support 180 includes memory shape polymer springs made from polymer thermoplastics such as, for example, amorphous thermoplastic polyetherimide or organic polymer thermoplastic from the polyaryletherketone family. The entire laminated ablation structure support 180 may be heat treated to achieve a non-persistent final spiral conformation. In an alternate embodiment, metallic springs, such as springs made from surgical stainless steel, may be used. The metallic springs are set in coils prior to lamination such that a persistent spiral conformation may be retained.

Figure 14:
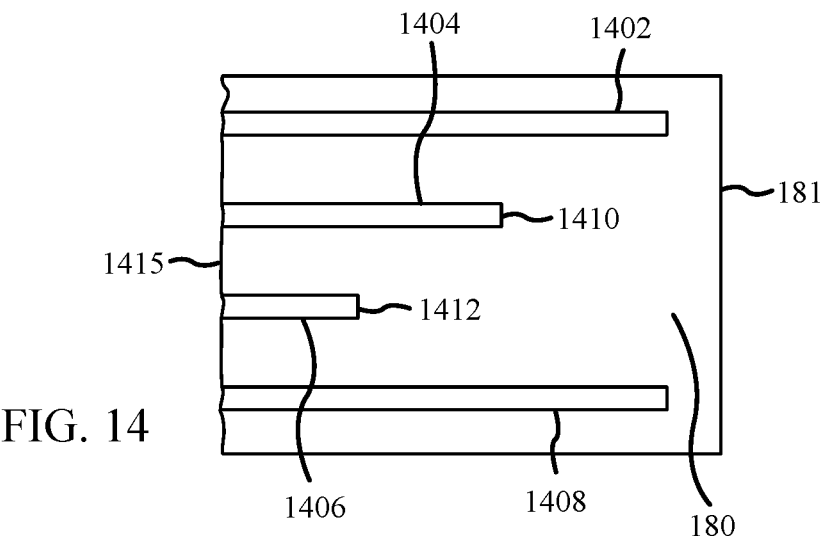
FIG. 14 is a plane view of an ablation structure of the ablation device of FIGS. 3-5 with variable-length springs.

Referring now to FIG. 14 through FIG. 17, various structures for localized reduction of spring density are shown in accordance with various embodiments. With reference now to FIG. 14, four springs of varying lengths 1402, 1404, 1406, 1408, are attached to the electrically insulated inside surface of the ablation structure support 180. The ablation structure support 180 may be an example of the ablation structure support 180 of FIGS. 1B, 6, 7, 8, 9, and/or 13. The variable-length springs 1402, 1404, 1406, 1408 are arranged such that the distal ends 1410, 1412 of one or more of the springs 1404, 1406 are not coterminous with the free end 181 of the ablation structure support 180. In some embodiments, a set of four springs includes two longer springs 1402, 1408 of equal length, one spring 1406 of shorter length, and one spring 1404 of a length less than the length of the longer springs 1402, 1408, but greater than the length of the shorter spring 1406. The spring density near the free end 181 of the ablation structure support 180 may be half that of the spring density near the bonded end 1415. In some instances, the spring density declines linearly from the bonded end 1415 to the free end 181 of the ablation structure support 180. Spring density at or near the free end 181 of the ablation structure support 180 may be directly related to the degree of clawing exhibited, where clawing refers to the tendency of the free end 181 of the ablation structure support 180 to return towards the initial spring radius.

Figure 15:
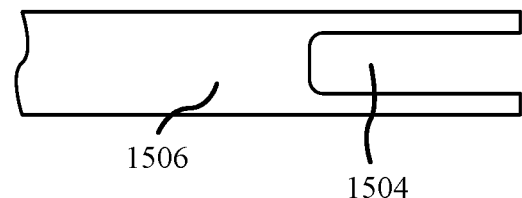
FIG. 15 is a plane view of a slotted spring of the ablation structure of FIG. 14.
Figure 16A:
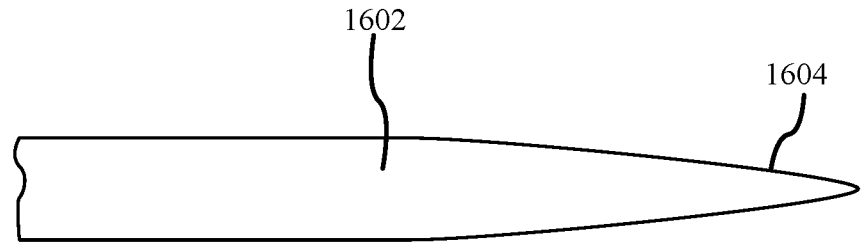
FIG. 16A is a plane view of a tapered spring of the ablation structure of FIG. 14.
Figure 16B:
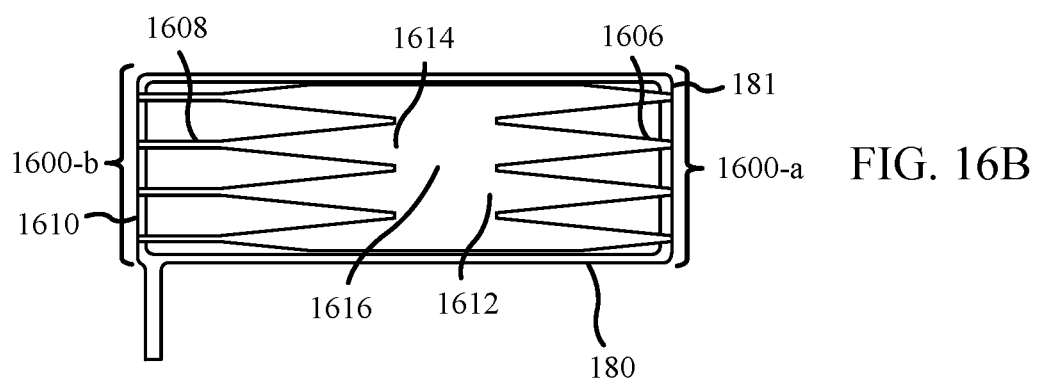
FIG. 16B is a plane view of an ablation structure of the ablation device of FIGS. 3-5 with tapered springs.
Figure 17:
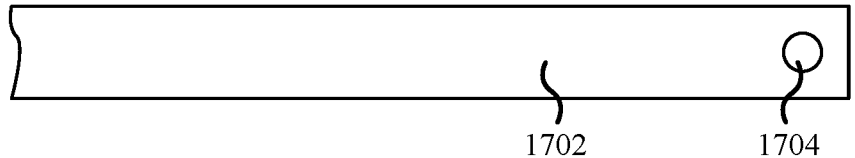
FIG. 17 is a plane view of a metal spring including a pinning hole of the ablation structure of FIG. 14.

With reference now to FIG. 15 through FIG. 17, localized spring density reduction may be obtained by reducing the amount of material at one or more locations along one or more springs. The spring 1506, 1602, 1702 may be examples of one or more of the springs described with reference to FIGS. 6-9, and/or 13-14. For example, referring to FIG. 15, a slot 1504 may be included at a distal portion of spring 1506, reducing the clawing force of the spring 1506 at or near the slotted region 1504. With reference to FIG. 16A, in some instances, localized spring density reduction is accomplished by tapering the distal portion 1604 of the spring 1602. Material may also be removed from the spring by techniques such as, for example, hole punching. Referring to FIG. 17, in some instances, one or more holes 1704 are punched at or near the distal end of one or more springs 1702. One or more of these techniques (i.e., variable width springs, tapered springs, slotted springs, and hole punched springs) may be combined such that a particular localized spring density is achieved.

Referring now to FIG. 16B, in certain embodiments, multiple polymeric springs 1600-a, 1600-b, each with a tapered portion, may be attached to the electrically insulated internal surface of the ablation structure support 180. The ablation structure support 180 may be an example of the ablation structure support 180 of FIGS. 1B, 6, 7, 8, and/or 9. The springs 1600-a, 1600-b may be arranged such that the first set of springs 1600-a are aligned adjacent to one another with the ends of the tapered portions 1606 abutting the free end of the ablation structure support 181, and the second set of springs 1600-b are aligned adjacent to one another with the ends of the tapered portions 1608 abutting the mounted end of the ablation structure support 1610. In some instances, the ends of the non-tapered spring portions 1612 of the first set of springs 1600-b are joined with ends of the non-tapered portion 1614 of the second set of springs 1600-b. In some embodiments, the location where the non-tapered ends join 1616 is at or near a middle portion of the ablation structure support 180. The spring density near the free end 181 and the mounted end 1610 of the ablation structure support 180 may each be less than half the spring density at or near the middle portion 1616 of the ablation structure support 180. In some instances, the spring density declines linearly in the direction of the free end 181 and the mounted end 1610 of the ablation structure support 181. In certain embodiments, the tapered portions 1608 of each of springs 1600-b taper to a defined density and extend to the mounted end 1610 of the ablation structure support 180 at the defined density. Spring density at or near the free end 181 and mounted end 1610 of the ablation structure support 180 may be directly related to the degree of clawing exhibited.

Figure 18:
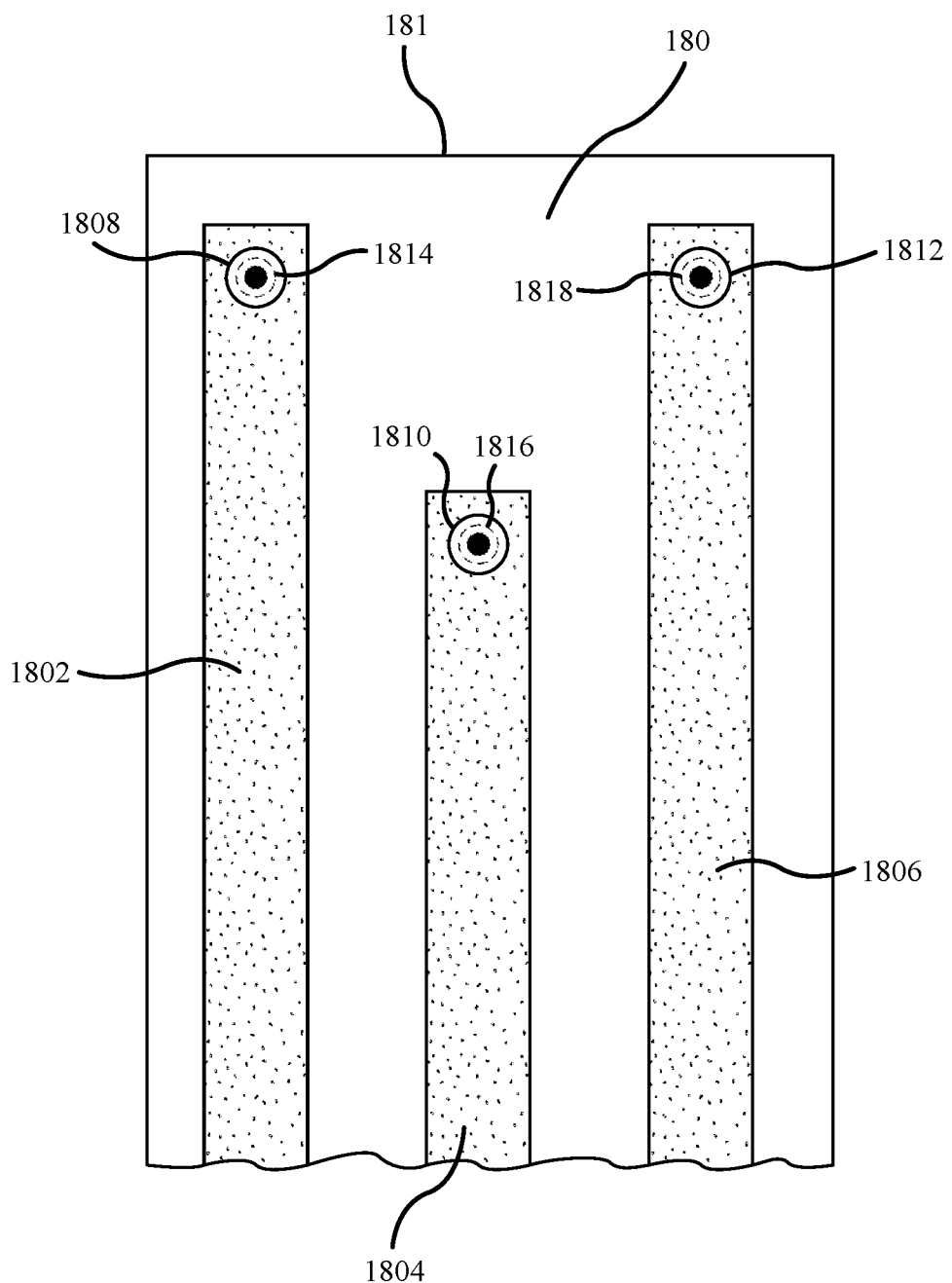
FIG. 18 is a plane view of an ablation structure of the ablation device of FIGS. 3-5 with pinned variable-length metal springs.

Referring now to FIG. 18, an ablation structure support 180 including metal springs 1802, 1804, 1806 is shown in accordance with various embodiments. The three metal springs 1802, 1804, 1806 shown may each include a hole 1814, 1816, 1818 at the distal end of the springs near the free edge 181 of the ablation structure support 180. The metal springs 1802, 1804, 1806 may be examples of one or more springs 602, 604, 606, 608 of FIG. 6, 720 of FIG. 7, 820 of FIG. 8, 916 of FIG. 9, 1304, 1305 of FIG. 13, and/or 1402, 1404, 1406, 1408 of FIG. 14. Fixture pins 1808, 1810, 1812 may pass through the spring holes 1814, 1816, 1818 and may each have a shaft circumference less than the spring holes 1814, 1816, 1818 and, in some instances, an external head circumference greater than the internal circumference of the spring holes 1814, 1816, 1818. The fixture pins 1808, 1810, 1812 may pass through the spring holes 1814, 1816, 1818 such that the ablation structure support 180 may be stretched into a flat configuration during lamination procedures. Such procedures are generally not utilized for shape memory polymer springs that are heat treated subsequent to lamination.

Figure 19A:
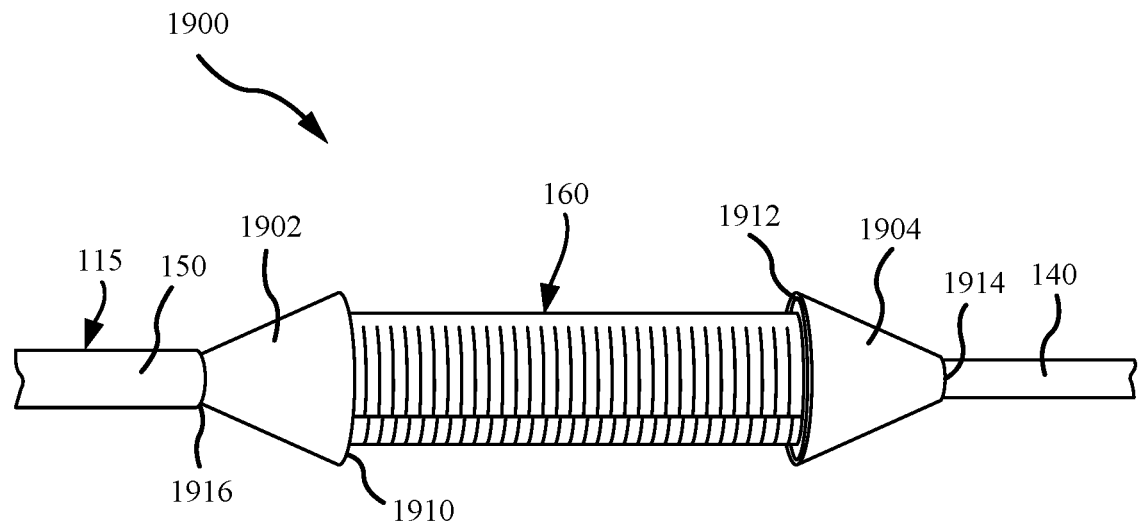
FIG. 19A is a perspective view of the ablation device of FIG. 4 in a furled/collapsed mode with proximal and distal protective cone elements.
Figure 19B:
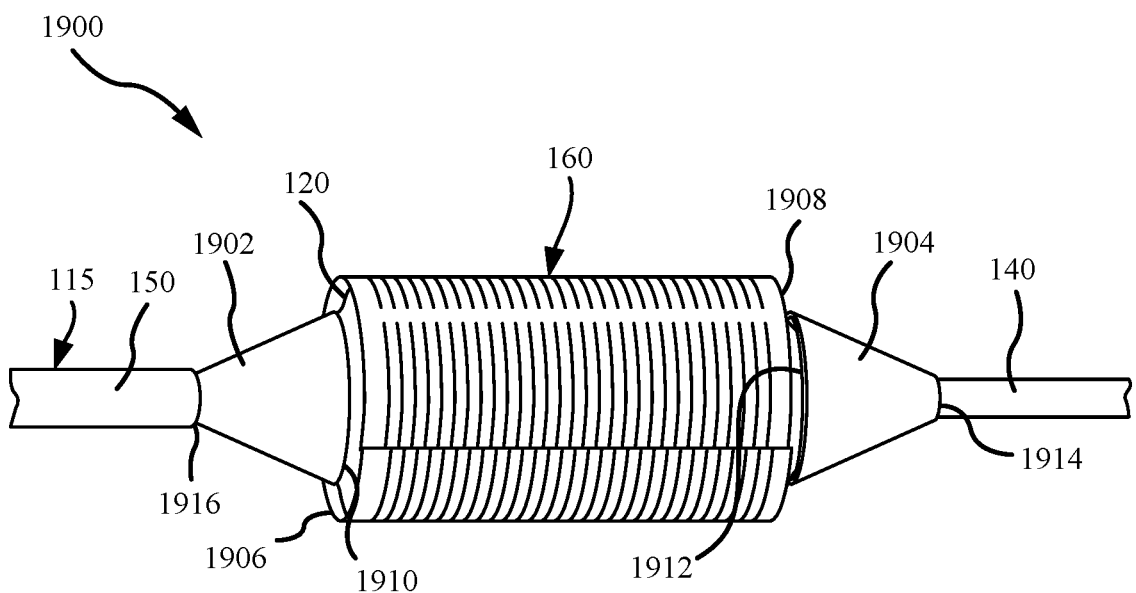
FIG. 19B is a perspective view of the ablation device of FIG. 5 in an unfurled/expanded mode with proximal and distal protective cone elements.

Referring now to FIG. 19A and FIG. 19B the distal portion of a general system 1900 for delivering treatment to a target treatment area is shown in a collapsed configuration (FIG. 19A) and in an expanded configuration (FIG. 19B) in accordance with various embodiments. System 1900 may be an example of systems 100, 100-a, 400, 600, 700, 800, or 900 described with reference to FIG. 1A, 1B, or 4-9, and may include a catheter 115, an expansion member 120 (shown in FIG. 19B only) coupled with the catheter 115, and an ablation structure 160. Conical protection elements 1902, 1904 may be positioned along the catheter 115 at the lateral edges 1906, 1908 of the ablation structure 160. The conical structures 1902, 1904 may be made of, for example, a flexible smooth polymer such as a high-density polyethylene. The larger openings 1910, 1912 of the conical structures 1902, 1904 are positioned facing the lateral edges 1906, 1908 of the ablation structure 160. The circumference at the large-diameter ends 1910, 1912 of the conical structures 1902, 1904 may be greater than the circumference of the collapsed ablation structure 160 such that the entire edge 1906, 1908 of the ablation structure 160 may be insertable in the larger openings 1910, 1912 of the conical structures 1902, 1904, thus preventing distention of the ablation structure 160 during removal and/or scraping of the lumen during insertion. The small-diameter end 1914 of the conical structure 1904 may have an internal circumference slightly greater than the external circumference of the distal portion 140 of the catheter 115 such that the conical structure 1904 may be slidably movable along the distal portion 140 of the catheter 115. In some embodiments, the small diameter end 1916 of the conical structure 1902 has an internal circumference less than the external circumference of portion 150 of catheter 115 such that the conical structure 1902 may not be slidably movable along the portion 150 of catheter 115. Referring now to FIG. 19B, the distal portion of system 1900 for delivering treatment to a target treatment area is shown in an expanded configuration in accordance with various embodiments. The conical structure 1904 may be moved slightly away from the ablation structure 160 such that the ablation structure 160 unfurls in response to the expansion of the expansion member 120 without being obstructed by the conical structures 1902, 1904.

Figure 20A:
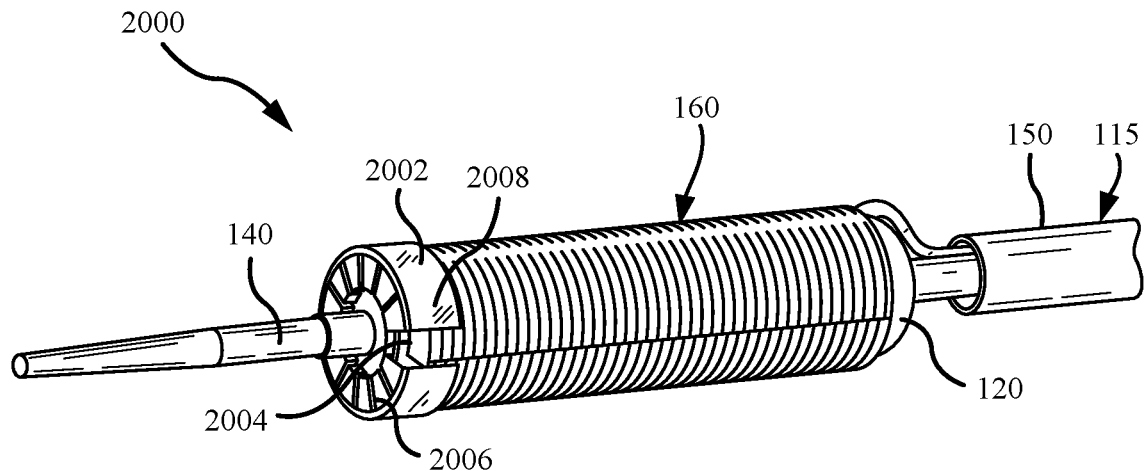
FIG. 20A is a perspective view of the ablation device of FIG. 4 in a furled/collapsed mode with a distal protective bumper element.
Figure 20B:
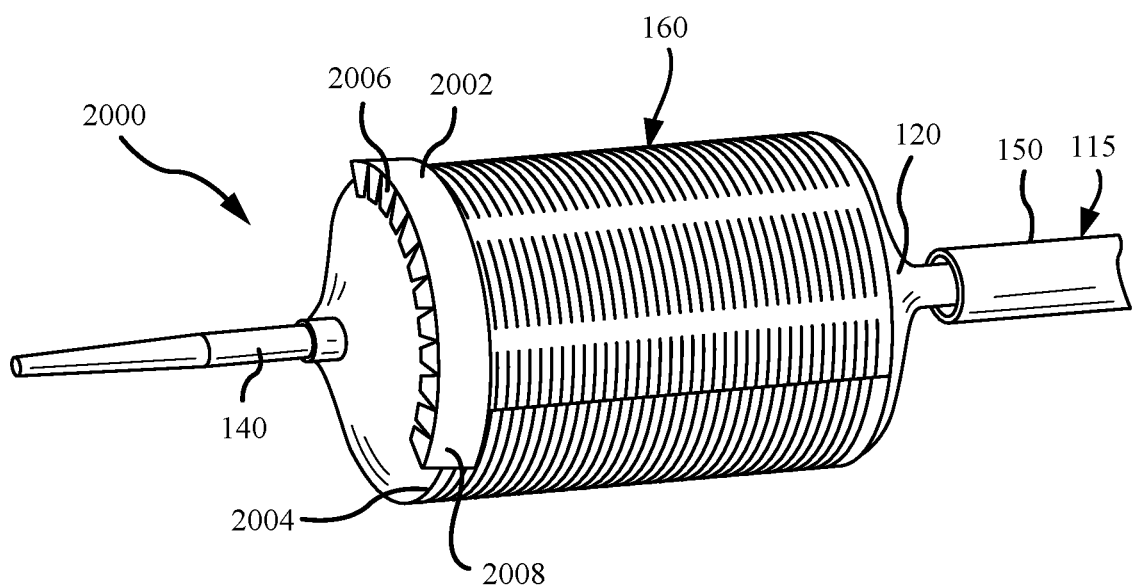
FIG. 20B is a perspective view of the ablation device of FIG. 5 in an unfurled/expanded mode with a distal protective bumper element.

Referring now to FIG. 20A and FIG. 20B, the distal portion of a general system 2000 for delivering treatment to a target treatment area is shown in a collapsed configuration (FIG. 20A) and in an expanded configuration (FIG. 20B) in accordance with various embodiments. System 2000 may be an example of systems 100, 100-a, 400, 600, 700, 800, 900, or 1900 described with reference to FIG. 1A, 1B, 4-9, or 19 and may include a catheter 115, an expansion member 120 coupled with the catheter 115, and an ablation structure 160. A bumper overhang structure 2002 may be bonded to a portion of the distal lateral edges 2004 of the ablation structure 160. The bumper overhang structure 2002 may be made of a highly flexible material such that the structure does not significantly impede the unfurling of the ablation structure 160 in response to the expansion of the expansion member 120. The overhang bumper structure 2002 may consist of an arcuate portion 2008 coplanar with, and bonded to, the surface of the ablation structure 160, and multiple adjacent trapezoid shaped structures 2006 extending perpendicularly from the arcuate portion 2008 radially towards the distal portion 140 of the catheter 115. The arc length of the arcuate portion 2008 may be such that a sufficient portion of the edge 2004 of the ablation structure 160 may be covered to prevent distention during removal and/or scraping of the lumen during insertion.

Figure 21:
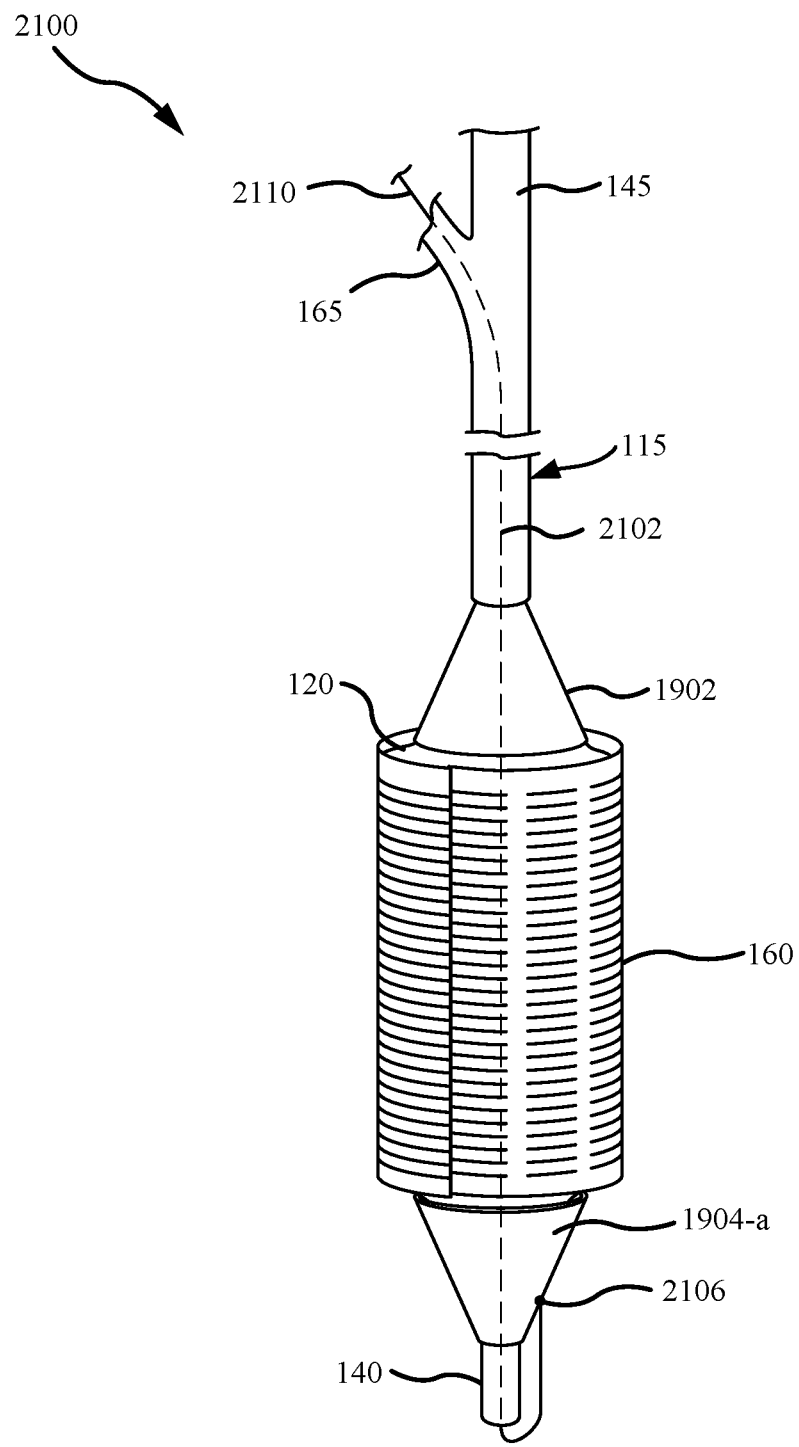
FIG. 21 is a perspective view of the ablation device of FIG. 20B in an unfurled/expanded mode with a tethered distal protective cone element.

Referring now to FIG. 21, the distal portion of a general system 2100 for delivering treatment to a target treatment area is shown in an expanded configuration in accordance with various embodiments. System 2100 may be an example of systems 100, 100-a, 400, 600, 700, 800, 900, 1900, or 2000 described with reference to FIG. 1A, 1B, 4-9, 19 or 20 and may include a catheter 115, an expansion member 120 coupled with the catheter 115, and an ablation structure 160. In some embodiments, a tethering structure 2102 extends internally all or a portion of the length of the catheter 115, out through distal portion 140, with the distal end 2106 of the tether 2102 attached to the distal, slidably movable, protection element 1904-a. The conical protection element 1904-a may be an example of the conical protection element 1904 described in connection with FIG. 19. The proximal end 2110 of the tethering structure 2102 extends out an opening 165 near the proximal portion 145 of the catheter 115 such that an operator can manipulate the tether 2102 and control the re-positioning of the slidably movable protection element 1904-a.

Figure 22:
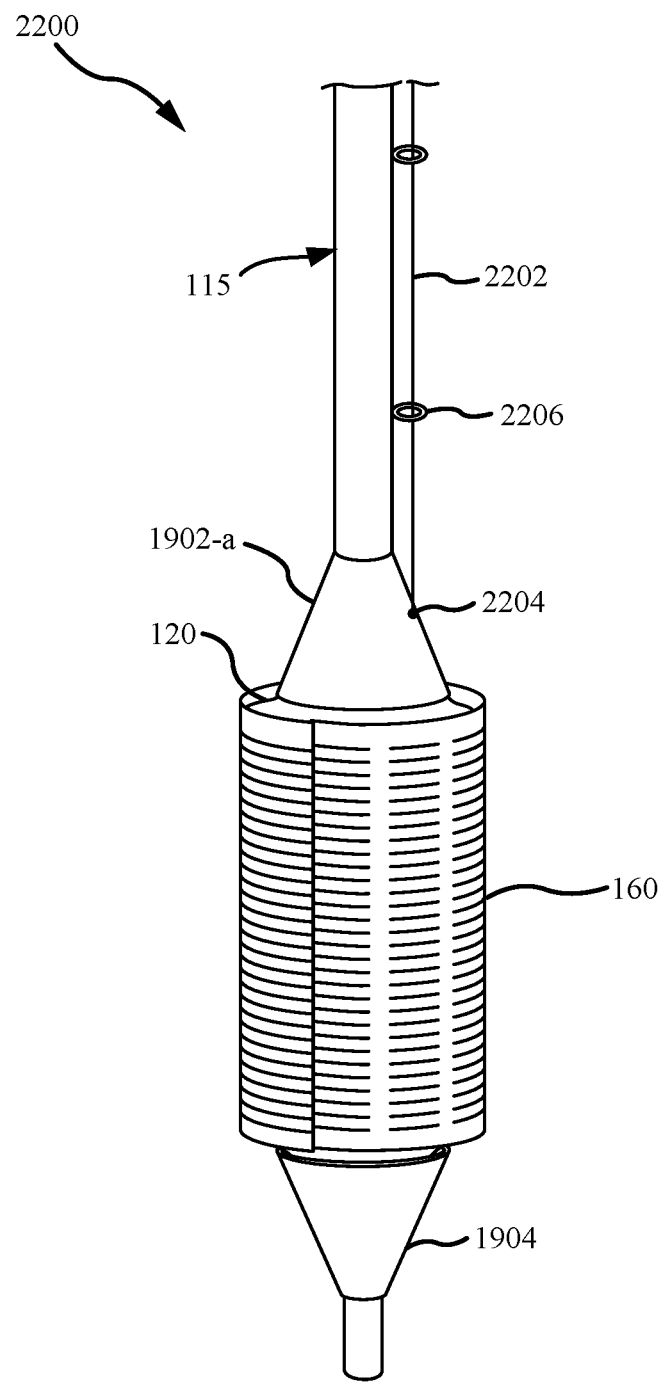
FIG. 22 is a perspective view of the ablation device of FIG. 20B in an expanded mode with tethered proximal and distal protective cone elements.

With reference now to FIG. 22, the distal portion of a general system 2200 for delivering treatment to a target treatment area is shown in an expanded configuration in accordance with various embodiments. System 2200 may be an example of systems 100, 100-a, 400, 600, 700, 800, 900, 1900, 2000, or 2100 described with reference to FIG. 1A, 1B, 4-9, or 19-21 and may include a catheter 115, an expansion member 120 coupled with the catheter 115, and an ablation structure 160. In some embodiments, a tethering structure 2202 extends externally all or part of the length of the of the proximal portion of the catheter 115 with the distal end 2204 of the tether 2202 attached to the proximal, slidably movable, protection element 1902-a. The conical protection element 1902-a may be an example of the conical protection element 1902 described with reference to FIG. 19. The tethering structure 2202 may be secured to the catheter 115 by, for example, one or more ring shaped structures 2206 mounted to the catheter 115 where such ringed structures 2206 have an internal circumference slightly greater than the circumference of the tethering structure 2202 allowing the tethering structure 2202 to slide freely in the one or more rings 2206. The distal end 2204 of the tethering structure 2202 may be accessible to the operator at the proximal portion 145 (not shown) of the catheter 115 such that an operator can manipulate the tether 2202 and control the re-positioning of the slidably movable protection element 1902-a.

Figure 23A:
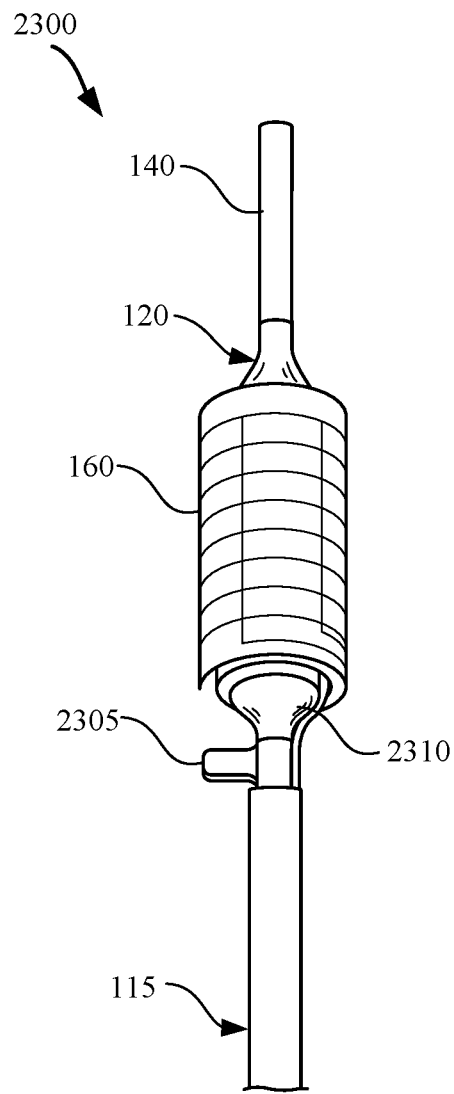
FIG. 23A is a perspective view of the ablation device of FIG. 4 in a furled/collapsed mode with a proximal raised bump element.
Figure 23B:
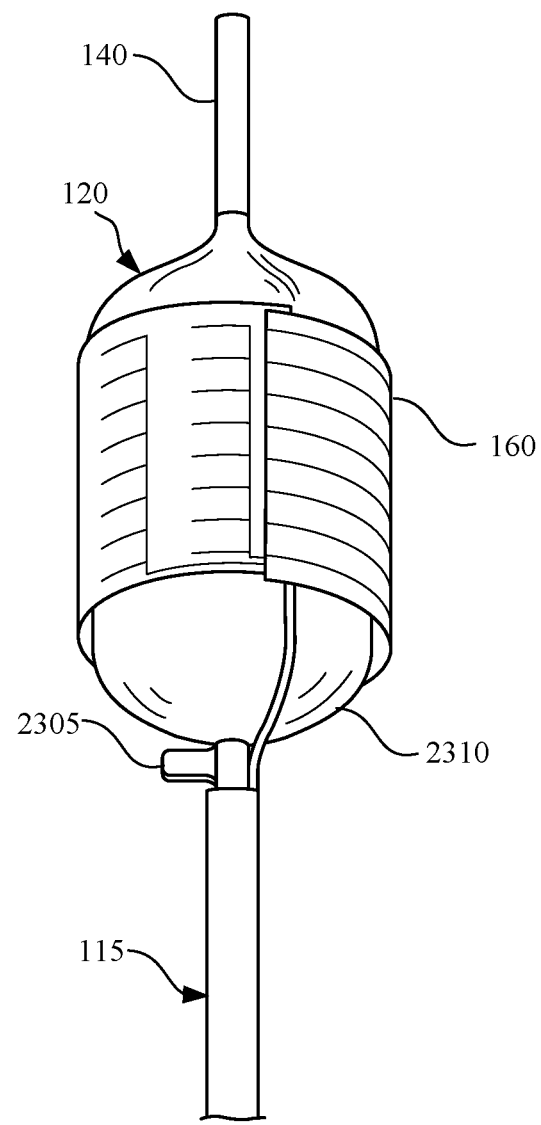
FIG. 23B is a perspective view of the ablation device of FIG. 5 in an unfurled/expanded mode with a proximal raised bump element.

With reference to FIG. 23A, the distal portion of a general system 2300 for delivering treatment to a target treatment area is shown in a collapsed/furled configuration in accordance with various embodiments. System 2300 may be an example of systems 100, 100-a, 400, 600, 700, 800, 900, 1900, 2000, 2100, or 2200 described with reference to FIG. 1A, 1B, 4-9, or 19-22 and may include a catheter 115, an expansion member 120 coupled with the catheter 115, and an ablation structure 160. As shown, in some embodiments, a raised bump 2305 is coupled with the catheter 115 and positioned near the proximal end 2310 of the expansion member 120. The raised bump 2305 may be made from any suitable polymeric material and may be adhered to or otherwise attached to the catheter 115. The raised bump 2305 may be configured to prevent proximal distension of ablation structure 160 along catheter 115 during insertion of the ablation structure 160 into a body lumen such as the esophagus. Accordingly, the height of the raised bump 2305 may be sufficiently large such that it protrudes away from catheter 115 further than the ablation structure 160 when the expansion member 120 is in a collapsed or unexpanded configuration. The raised bump 2305 may be an example of a protection element as described with reference to FIGS. 19-22. Referring to FIG. 23B, the expansion member 120 and ablation structure 160 illustrated in FIG. 23A is shown in an expanded/unfurled configuration in accordance with various embodiments.

Figure 24:
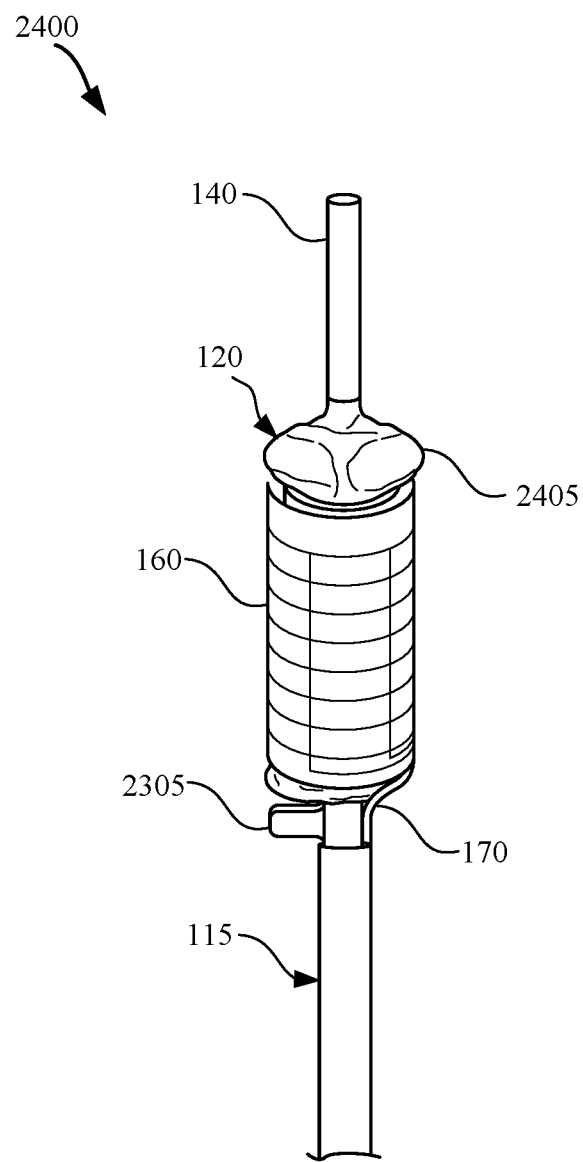
FIG. 24 is a perspective view of the ablation device of FIG. 4 in a furled/collapsed mode.

With reference to FIG. 24, the distal portion of a general system 2400 for delivering treatment to a target treatment area is shown in a collapsed/furled configuration in accordance with various embodiments. System 2400 may be an example of systems 100, 100-a, 400, 600, 700, 800, 900, 1900, 2000, 2100, 2200, or 2300 described with reference to FIG. 1A, 1B, 4-9, or 19-23 and may include a catheter 115, an expansion member 120 coupled with the catheter 115, and an ablation structure 160. As shown, the expansion member 120 may include a bunched up portion 2405 positioned near the distal end 140 of the catheter 115. The bunched up portion 2405 of expansion member 120 may be configured to prevent distension of the ablation structure 160 in a distal direction along the catheter 115 while the ablation structure 160 is being removed from a body lumen. Accordingly, the bunched up portion 2405 may be configured to have an average diameter that is larger than the diameter of the ablation structure 160 in an unexpanded or collapsed configuration. The bunched up portion 2405 may be an example of a protection element as described with reference to FIGS. 19-22.

The expansion member 120 may be modified in a variety of ways to create the bunched up portion 2405. For example, the expansion member 120 may be designed to have a steep taper angle on the distal end of the expansion member 120. The steep taper angle will cause the distal portion of the expansion member 120 to bunch up while unexpanded, thus forming a bunched up portion 2405. Additionally or alternatively, the expansion member 120 may include multiple layers of material near the distal end to form the bunched up portion 2405. Accordingly, the distal portion of the expansion member 120 may be thicker than the rest of expansion member 120. The multiple layers of expansion member 120 may be thermally fused together or may be joined through adhesives or mechanical fastening elements.

For example, in various embodiments the expansion member 120 is a balloon formed from a two-step blow-molding process. The first step of the blow-molding process may include forming a first balloon and then cutting off the distal end of the balloon. This cut-off portion may be then added back into the balloon mold while a second balloon is being formed. In particular, the cut-off portion is placed in the mold such that it overlaps the distal portion of the second balloon as it is being formed. By overlapping the cut-off portion of the first balloon with the distal portion of the second balloon, the distal portion of the second balloon will be thicker than the rest of the balloon material. Accordingly, when the balloon is in a deflated or unexpanded state, the distal portion may form a bunched up portion 2405 due to the excess material. It may be appreciated that the size of the bunched up portion 2405 may be tailored by modifying the taper angle of the distal portion of expansion member 120 in addition to the number and thickness of additional layers of material near the distal portion of expansion member 120.

Figure 25:
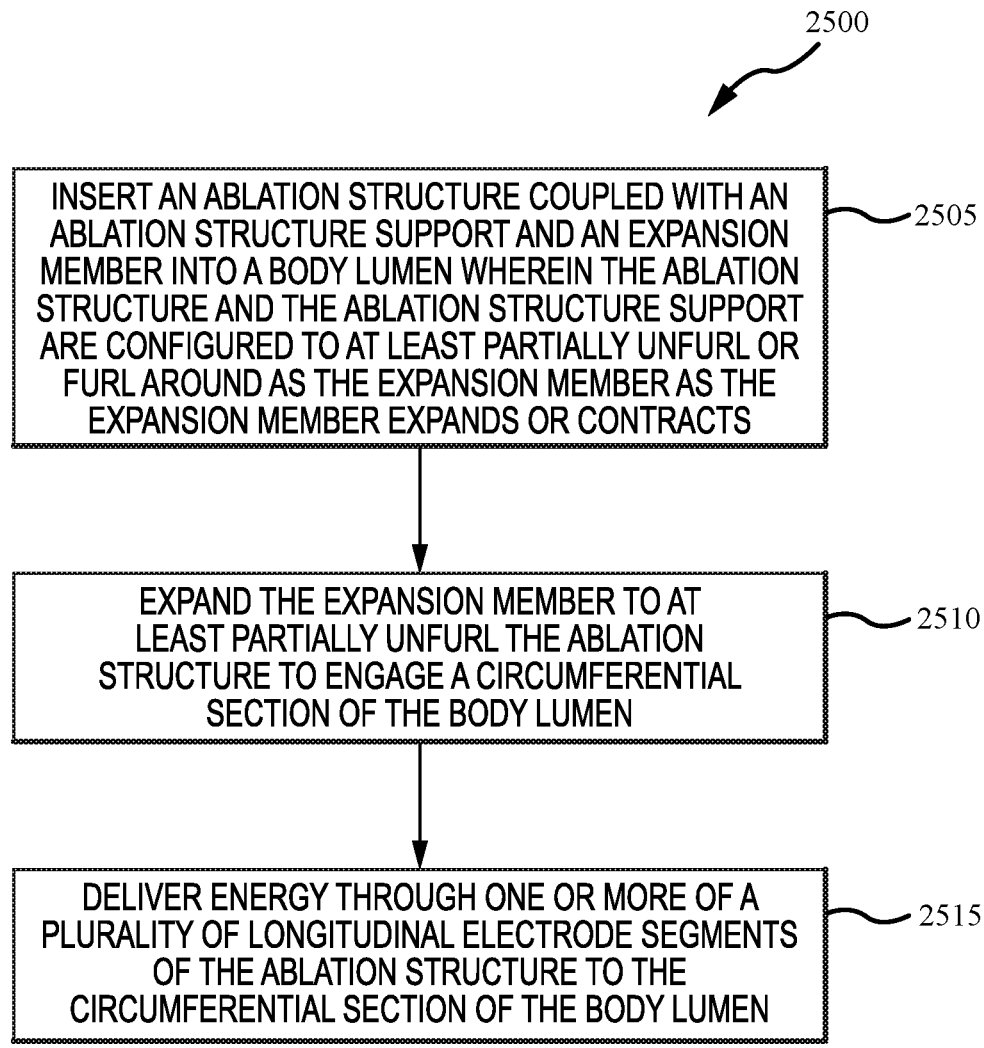
FIG. 25 is a flow diagram illustrating a method for providing treatment to a target site area according to various embodiments.

With reference to FIG. 25, a general method 2500 of using various embodiments of the systems and/or devices described herein is shown in accordance with various embodiments. For example, method 2500 may be implemented utilizing the various embodiments of system 100, power source 105, hand-held compressor 112, expansion member 120, ablation structure 160, ablation structure support 180, protection elements 1902, 1904, 2002 and/or other devices and/or components. At block 2505, the ablation structure 160 coupled with the ablation structure support 180 and the expansion member 120 may be inserted into the body lumen. The ablation structure 160 coupled with the ablation structure support 180, in combination, may unfurl in response to the expansion of the expansion member 120, and furl in response to the contraction of the expansion member 120. A guide assembly 165 may be used such that the expansion member 120 may be passed over the guide assembly 165 delivering the ablation structure 160 to a target treatment area inside the body lumen.

At block 2510, the expansion member 120 may be expanded such that the ablation structure 160 coupled with the ablation structure support 180, in combination, unfurl and engage a circumferential section of the body lumen. In some instances, the expansion member 120 includes a compliant balloon. In some embodiments, the power source 105 and/or the hand-held compressor 112 may be used to expand the expansion member 120.

At block 2515, energy may be delivered through the ablation structure 160 to first part of a circumferential treatment area of the body lumen. In some embodiments, the ablation structure 160 includes two or more longitudinal electrodes or longitudinal electrode zones of varying widths. In some embodiments, the ablation structure 160 includes two or more longitudinal electrodes or longitudinal electrode zones configured to be selectively enabled or selectively disabled. In certain instances, the ablation structure 160 includes a bipolar electrode array.

Figure 26:
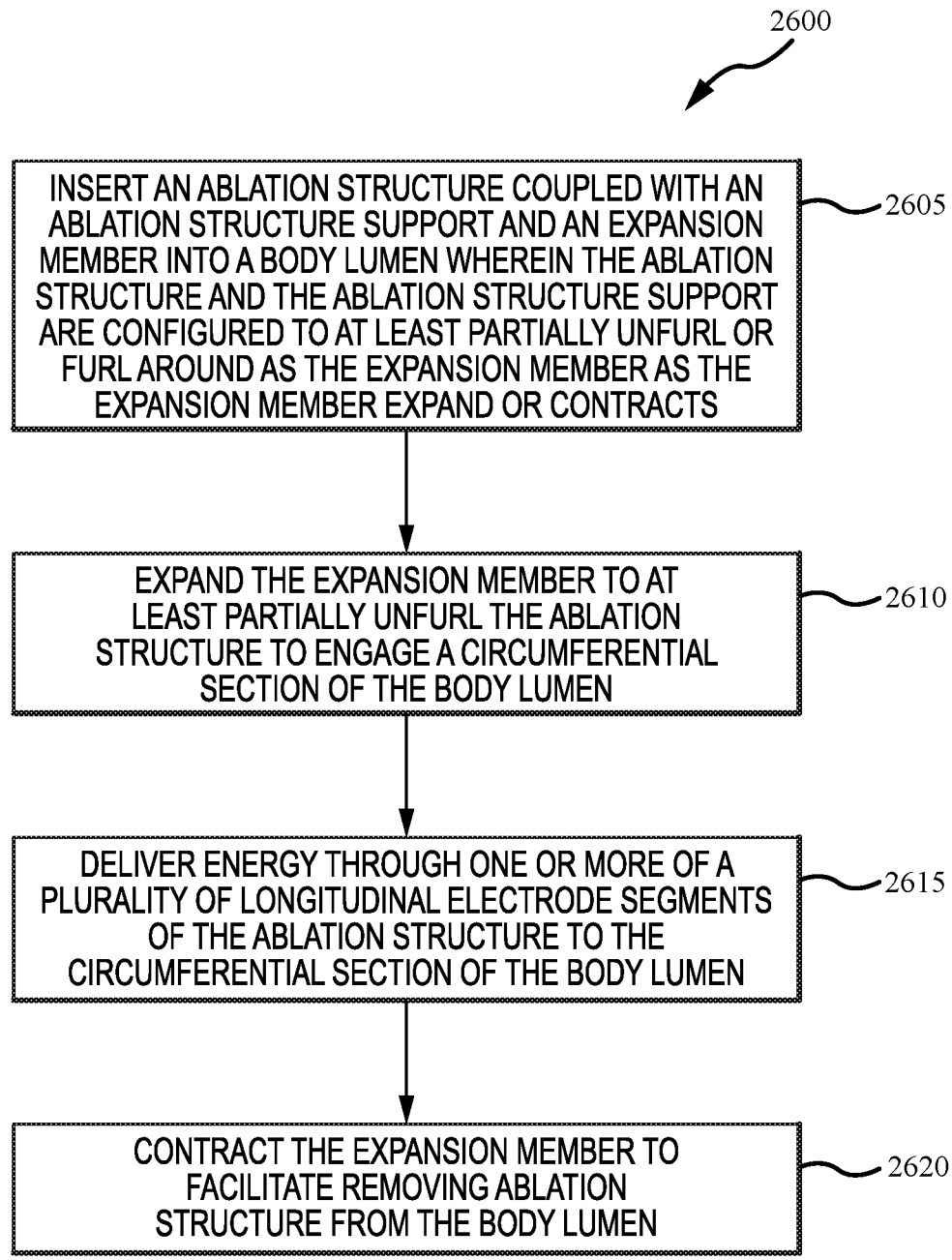
FIG. 26 is a flow diagram illustrating a method for providing treatment to a target site area according to various embodiments.

With reference to FIG. 26, a general method 2600 of using various embodiments of the systems and/or devices described herein is shown in accordance with various embodiments. Method 2600 may be an example of method 2500 described with reference to FIG. 25. For example, blocks 2605, 2610, and 2615 may be examples of the methods described in blocks 2505, 2510, and 2515 of method 2500. Furthermore, at block 2620, the expansion member 120 may be contracted such that the ablation structure 160 coupled with the ablation structure support 180 including one or more springs, in combination, furls and disengages a circumferential section of the body lumen. For example, method 2600 may be implemented utilizing the various embodiments of system 100, power source 105, hand-held compressor 112, expansion member 120, ablation structure 160, ablation structure support 180, springs 1506, 1602, 1702, protection elements 1902, 1904, 2002, and/or other devices and/or components. In some instances, the expansion member 120 includes a compliant balloon. In some embodiments, a vacuum is used to fully contract the expansion member 120. In some instances, the one or more springs include a constant force spring.

Figure 27:
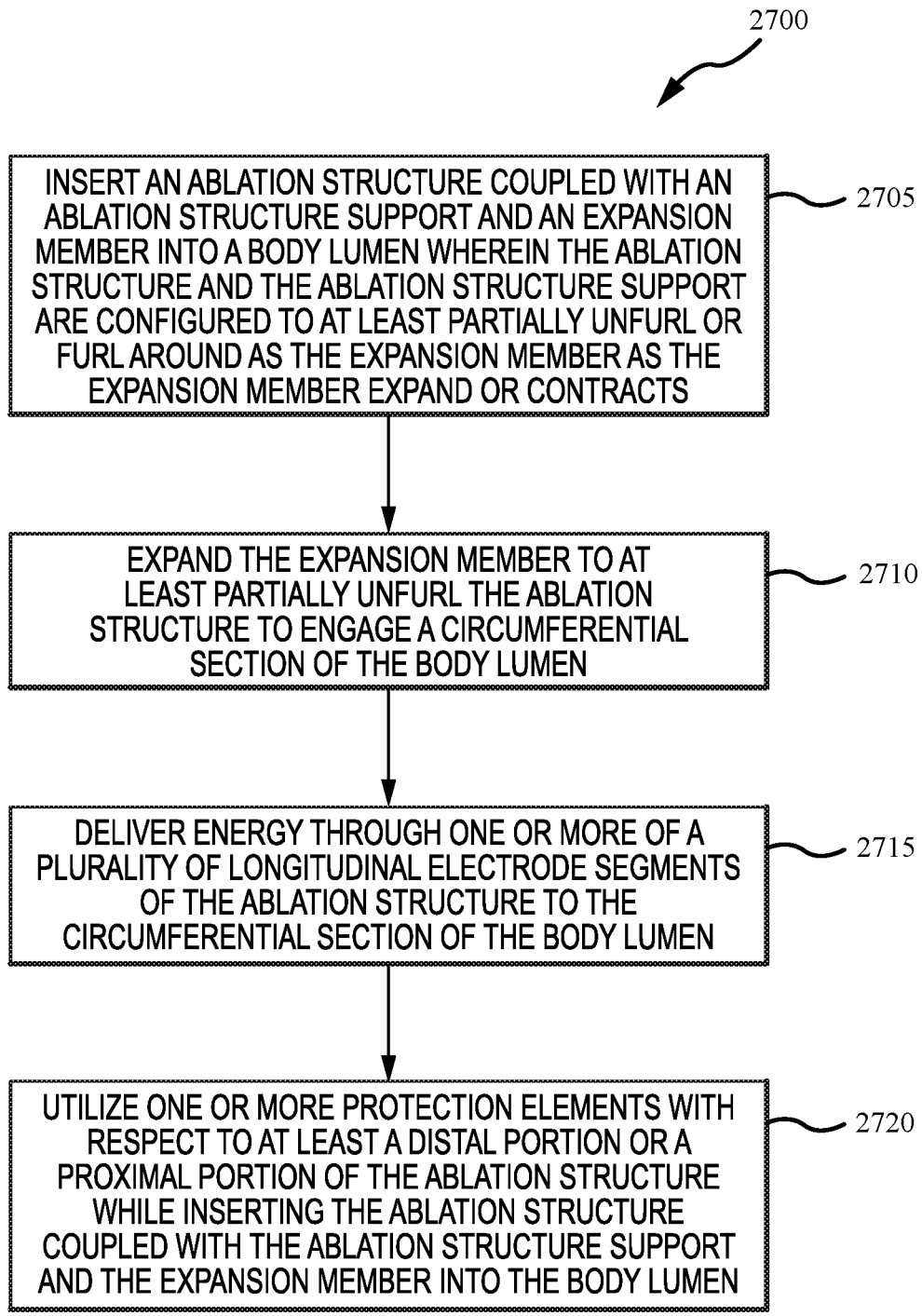
FIG. 27 is a flow diagram illustrating a method for providing treatment to a target site area using an expansion member including one or more protection elements according to various embodiments.

With reference to FIG. 27, a general method 2700 of using various embodiments of the systems and/or devices described herein is shown in accordance with various embodiments. Method 2700 may be an example of method 2500 described with reference to FIG. 25. For example, blocks 2705, 2710, and 2715 may be examples of the methods described in blocks 2505, 2510, and 2515 of method 2500. Furthermore, at block 2720, one or more protection elements may be utilized during the insertion of the ablation structure coupled with the ablation structure support 180 and the expansion member 120 into the body lumen. For example, method 2700 may be implemented utilizing the various embodiments of system 100, power source 105, hand-held compressor 112, expansion member 120, ablation structure 160, ablation structure support 180, springs 1506, 1602, 1702, protection elements 1902, 1904, 2002, and/or other devices and/or components. One or more protection elements are positioned at the distal portion, proximal portion or both of the ablation structure 160. These protection elements may, for example include conical shaped structures, bumper shaped structures, a raised bump 2305 coupled with the catheter 115, or a portion 2405 of the expansion member 120 that is bunched up, each positioned such that they prevent distension of the ablation structure 160 and/or prevent the leading edge of the ablation structure from scraping the lumen wall during insertion. In some embodiments of the method, one or more of the protection elements are moved away from the ablation structure after the ablation structure is positioned.

Figure 28:
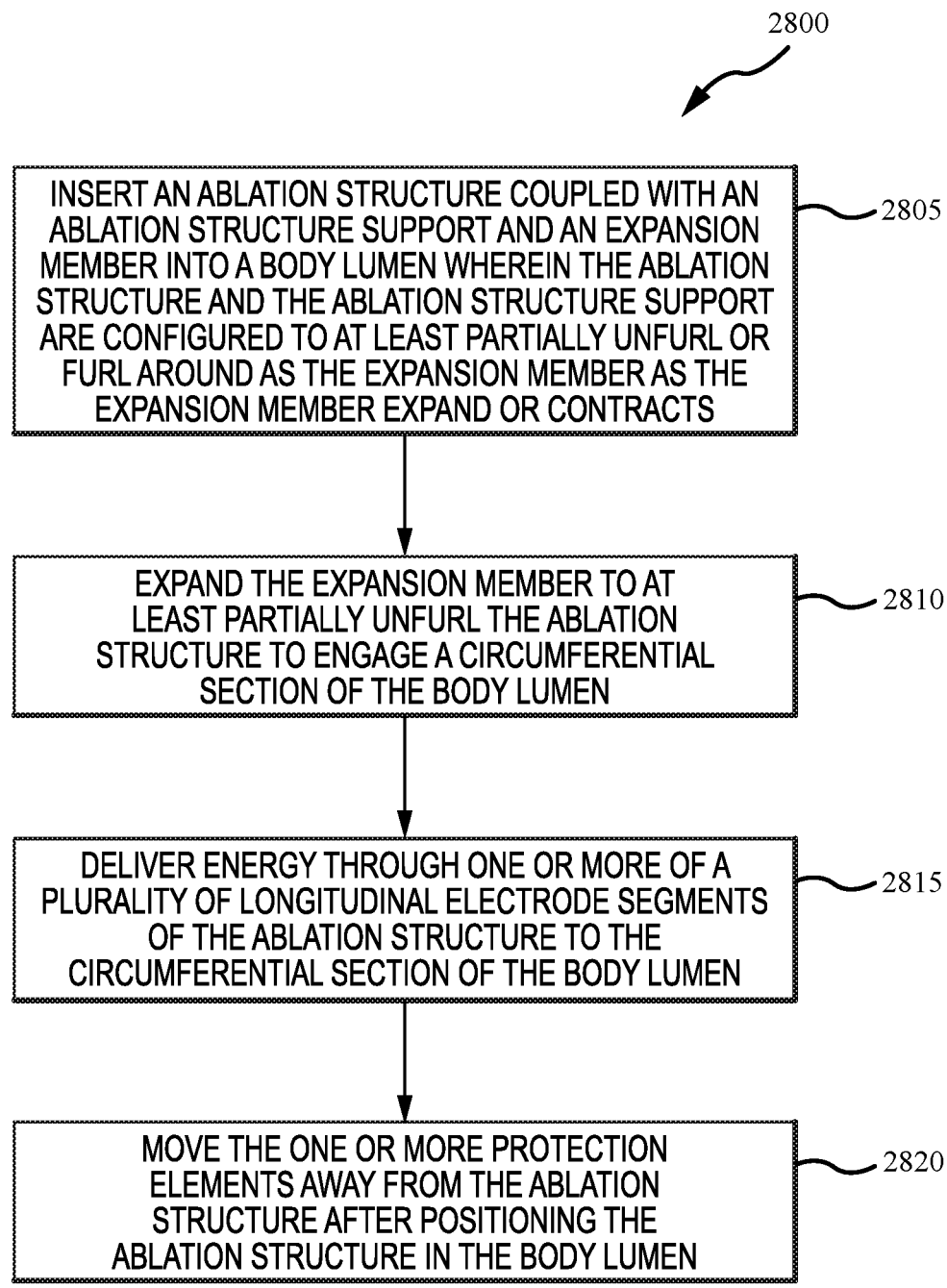
FIG. 28 is a flow diagram illustrating a method for providing treatment to a target site area using an expansion member including one or more movable protection elements according to various embodiments.

With reference to FIG. 28, a general method 2800 of using various embodiments of the systems and/or devices described herein is shown in accordance with various embodiments. Method 2800 may be an example of method 2500 described with reference to FIG. 25. For example, blocks 2805, 2810, and 2815 may be examples of the methods described in blocks 2505, 2510, and 2515 of method 2500. Furthermore, at block 2820, one or more protection elements are moved distally from the lateral edge of the ablation structure 160 subsequent to positioning the ablation structure 160 in the body lumen. For example, method 2800 may be implemented utilizing the various embodiments of system 100, power source 105, hand-held compressor 112, expansion member 120, ablation structure 160, ablation structure support 180, springs 1506, 1602, 1702, protection elements 1902, 1904, tethers 2102, 2202, and/or other devices and/or components. Moving one or more protection elements after positioning of the ablation structure 160 facilitates unobstructed unfurling of the ablation structure 160 coupled with the ablation structure support 180, in combination, while continuing to prevent distension of the ablation structure 160 and/or preventing the leading edge of the ablation structure 160 from scraping the lumen wall during insertion.

Figure 29:
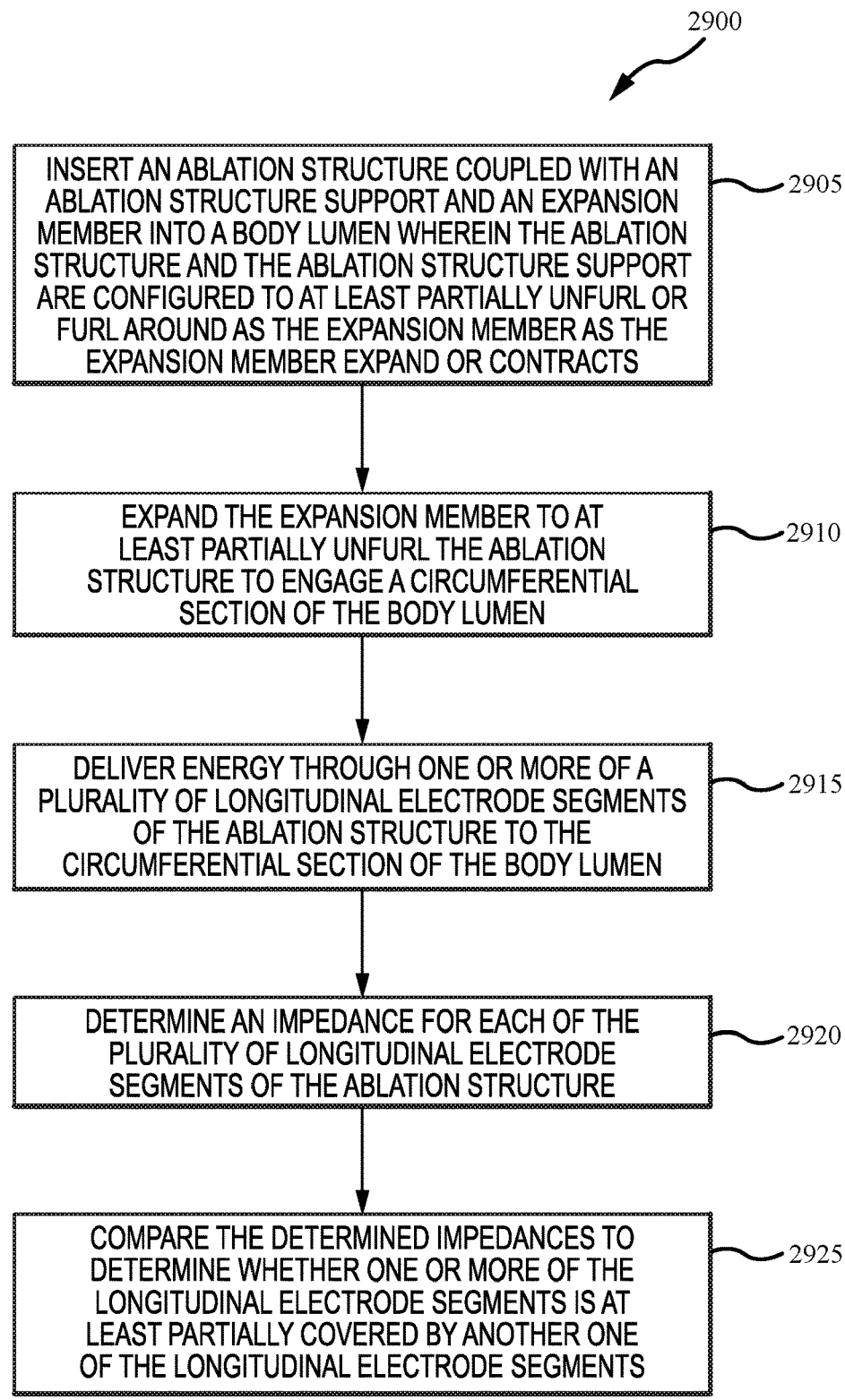
FIG. 29 is a flow diagram illustrating a method for providing treatment to a target site area according to various embodiments.

With reference to FIG. 29, a general method 2900 of using various embodiments of the systems and/or devices described herein is shown in accordance with various embodiments. Method 2900 may be an example of method 2500 described with reference to FIG. 25. For example, blocks 2905, 2910, and 2915 may be examples of the methods described in blocks 2505, 2510, and 2515 of method 2500. Furthermore, at block 2920, an impedance level may be determined for each longitudinal electrode or longitudinal electrode zone. For example, method 2900 may be implemented utilizing the various embodiments of system 100, power source 105, hand-held compressor 112, expansion member 120, ablation structure 160, ablation structure support 180, springs 1506, 1602, 1702, protection elements 1902, 1904, 2002, and/or other devices and/or components. In some instances, measurements are taken sequentially prior to enabling a given longitudinal electrode or longitudinal electrode zone, starting with the longitudinal electrode or longitudinal electrode zone adjacent to the free edge of the ablation structure. In another embodiment, the rate of impedance change is measured during ablation. In some instances, at block 2925, the starting impedance of the current longitudinal electrode or longitudinal electrode zone in the sequence of electrodes or electrode zones is compared to previously obtained impedance starting impedance levels for prior longitudinal electrodes or longitudinal electrode zones in the sequence of electrodes or electrode zones. In some instances, the rate of impedance change during ablation for the current longitudinal electrode or longitudinal electrode zone is compared to previously obtained impedance change rates for the current patient and/or from previous patients.

Figure 30:
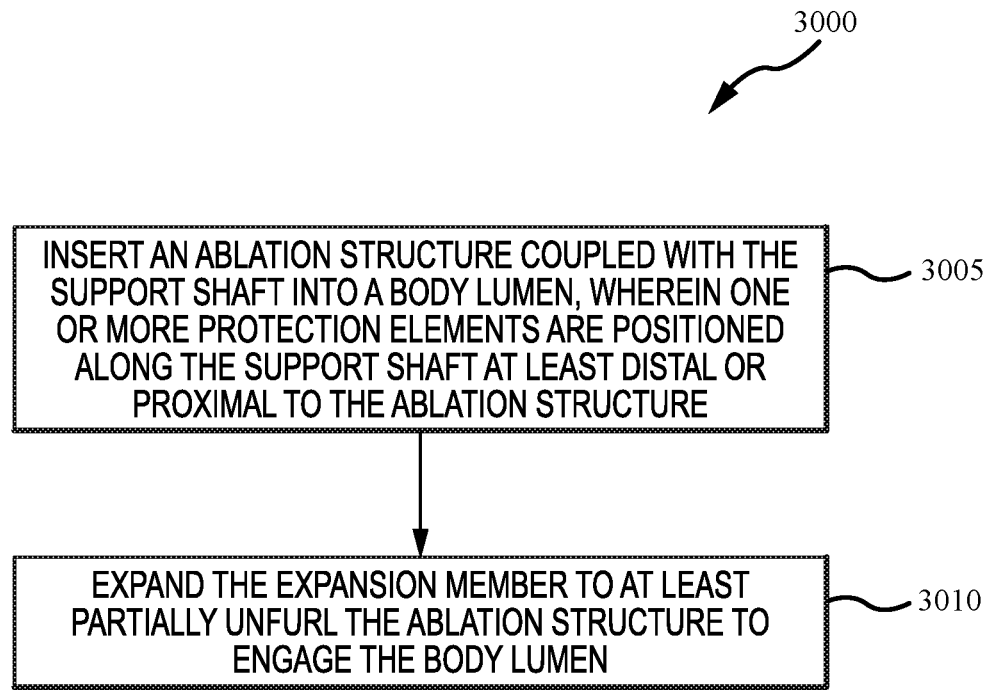
FIG. 30 is a flow diagram illustrating a method for providing treatment to a target site area using an expansion member including one or more protection elements according to various embodiments.

With reference to FIG. 30 a general method 3000 of using various embodiments of the systems and/or devices described herein is shown in accordance with various embodiments. For example, method 3000 may be implemented utilizing the various embodiments of system 100, expansion member 120, ablation structure 160, ablation structure support 180, protection elements 1902, 1904, 2002 and/or other devices and/or components. At block 3005, the ablation structure 160 coupled with the ablation structure support 180 and the expansion member 120 are inserted into the body lumen. The one or more protection elements may be positioned at the distal portion, proximal portion or both of the ablation structure 160. These protection elements may, for example, include conical shaped structures, overhanging bumper shaped structures, a raised bump 2305 coupled with the catheter 115, or a portion 2405 of the expansion member 120 that is bunched up, each positioned such that they prevent distension of the ablation structure 160 and/or prevent the leading edge of the ablation structure 160 from scraping the lumen wall during insertion. In certain instances, the ablation structure 160 includes a furled bipolar electrode array.

At block 3010, the expansion member 120 may be expanded such that the ablation structure 160 coupled with the ablation structure support 180, in combination, may unfurl and engage a circumferential section of the body lumen. In some instances, the expansion member 120 includes a compliant balloon. In some embodiments, the power source 105 and/or the hand-held compressor 112 are used to expand the expansion member 120.

Figure 31:
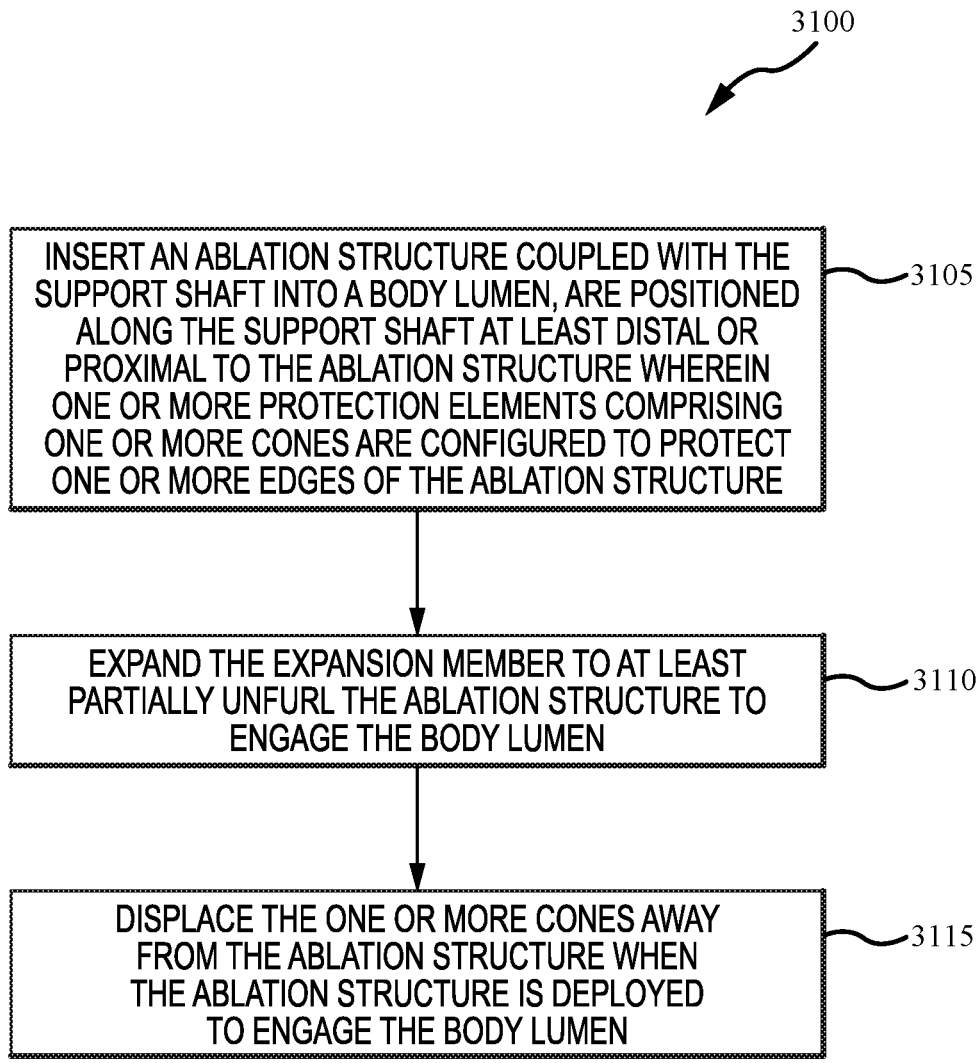
FIG. 31 is a flow diagram illustrating a method for providing treatment to a target site area using an expansion member including one or more protection elements according to various embodiments.

With reference to FIG. 31, a general method 3100 of using various embodiments of the systems and/or devices described herein is shown in accordance with various embodiments. Method 3100 may be an example of method 3000 described with reference to FIG. 30. For example, blocks 3105 and 3110 may be examples of the methods described in blocks 3005, and 3010 of method 3000. Furthermore, at block 3115, one or more protection elements may be displaced distally from the lateral edge of the ablation structure 160 subsequent to positioning the ablation structure in the body lumen. For example, method 3100 may be implemented utilizing the various embodiments of system 100, expansion member 120, ablation structure 160, ablation structure support 180, protection elements 1902, 1904 and/or other devices and/or components. Moving one or more protection elements after positioning of the ablation structure 160 facilitates unobstructed unfurling of the ablation structure 160 coupled with the ablation structure support 180, in combination, while continuing to prevent distension of the ablation structure 160 and/or preventing the leading edge of the ablation structure from scraping the lumen wall during insertion.

Figure 32:
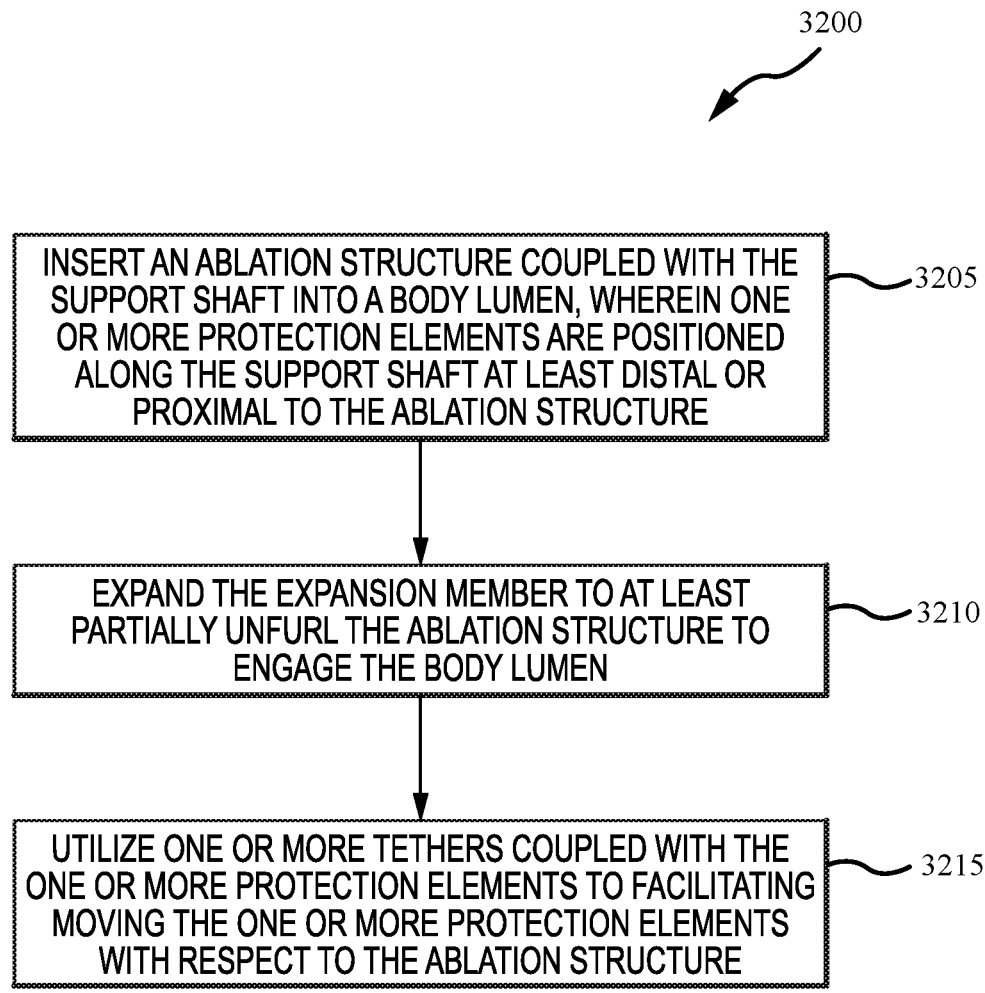
FIG. 32 is a flow diagram illustrating a method for providing treatment to a target site area using an expansion member including one or more tethered movable protection elements according to various embodiments.

With reference to FIG. 32, a general method 3200 of using various embodiments of the systems and/or devices described herein is shown in accordance with various embodiments. Method 3200 may be an example of method 3000 described with reference to FIG. 30. For example, blocks 3205 and 3210 may be examples of the methods described in blocks 3005, and 3010 of method 3000. Furthermore, at block 3215, one or more protection elements may be moved relative to the ablation structure 160 through the use of one or more tethering structures coupled to one or more of the protective elements. For example, method 3200 may be implemented utilizing the various embodiments of system 100, expansion member 120, ablation structure 160, ablation structure support 180, protection elements 1902, 1904, tethers 2102, 2202, and/or other devices and/or components. In some embodiments, the tethering structures extend upward from the protection elements along the length of the catheter such that an operator may manipulate the tether and control the re-positioning of one or more of the protective elements.

The foregoing description provides examples, and is not intended to limit the scope, applicability or configuration of the various embodiments. Rather, the description and/or figures provide those skilled in the art with an enabling description for implementing various embodiments. Various changes may be made in the function and arrangement of elements.

Thus, various embodiments may omit, substitute, or add various procedures or components as appropriate. For instance, it should be appreciated that the methods may be performed in an order different than that described, and that various steps may be added, omitted or combined. Also, aspects and elements described with respect to certain embodiments may be combined in various other embodiments. It should also be appreciated that the following systems, methods, and devices, may individually or collectively be components of a larger system, wherein other procedures may take precedence over or otherwise modify their application.

The foregoing descriptions of specific embodiments have been presented for purposes of illustration and description. They are not intended to be exhaustive or to limit the invention to the precise forms disclosed, and obviously many modifications and variations are possible in light of the above teaching. The embodiments were chosen and described in order to explain the principles of the various embodiments and its practical application, to thereby enable others skilled in the art to utilize the various embodiments with various modifications as are suited to the particular use contemplated. It is intended that the scope of the various embodiments be defined by the Claims appended hereto and their equivalents.

What is claimed is:

1. An ablation device for treatment of tissue in body lumens with varying sizes, the device comprising:
    a catheter;
    an expansion member coupled with the catheter; and
    an ablation structure coupled with the expansion member, wherein the ablation structure is configured to furl around the expansion member to a furled configuration as the expansion member contracts and unfurl around the expansion member to an unfurled configuration as the expansion member expands; and
    one or more support elements positioned along the catheter at least distal or proximal to the ablation structure, wherein the one or more support elements are configured to prevent the ablation structure from extending along the catheter during at least deployment into a body lumen or removal from the body lumen.

2. The ablation device of claim 1, wherein a radial dimension of the one or more support elements is greater than a radial dimension of the ablation structure in the furled configuration.

3. The ablation device of claim 1, wherein the one or more support elements comprises one or more cones configured to protect one or more edges of the ablation structure.

4. The ablation device of claim 3, wherein the one or more cones are configured to move away from the ablation structure when the ablation structure unfurls to contact the body lumen.

5. The ablation device of claim 3, further comprising:
    one or more tethers coupled to the one or more cones, wherein the one or more tethers are configured to move the one or more cones away from the ablation structure.

6. The ablation device of claim 1, wherein the one or more support elements are configured to prevent the ablation structure from damaging a surface of the body lumen during at least deployment into the body lumen or removal from the body lumen.

7. The ablation device of claim 1, wherein the one or more support elements comprises one or more bumpers coupled with one or more edges of the ablation structure.

8. The ablation device of claim 7, wherein the one or more bumpers are bonded to at least a portion of a distal edge of the ablation structure.

9. The ablation device of claim 8, wherein the one or more bumpers overhang the distal edge of the ablation structure inwards towards the catheter.

10. The ablation device of claim 1, wherein the one or more support elements proximal to the ablation structure comprises a raised bump coupled with the catheter.

11. The ablation device of claim 1, wherein the one or more support elements distal to the ablation structure comprises a bunched up portion of the expansion member configured to bunch up when the expansion member is in the furled configuration.

12. The ablation device of claim 11, wherein a diameter of the bunched up portion exceeds a diameter of the ablation structure in the furled configuration.

13. A method for treatment of tissue in body lumens with varying sizes, the method comprising:
    inserting an ablation structure coupled with an expansion member into a body lumen, wherein one or more support elements are positioned along a catheter at least distal or proximal to the ablation structure, wherein the one or more support elements are configured to prevent the ablation structure from extending along the catheter during at least deployment into the body lumen or removal from the body lumen; and
    expanding the expansion member to at least partially unfurl the ablation structure to engage the body lumen, wherein the ablation structure is configured to furl around the expansion member to a furled configuration as the expansion member contracts and unfurl around the expansion member to an unfurled configuration as the expansion member expands.

14. The method of claim 13, wherein a radial dimension of the one or more support elements is greater than a radial dimension of the ablation structure in the furled configuration.

15. The method of claim 13, wherein the one or more support elements comprises one or more cones configured to protect one or more edges of the ablation structure.

16. The method of claim 15, further comprising:
    moving the one or more cones away from the ablation structure when the ablation structure unfurls to contact the body lumen.

17. The method of claim 16, wherein moving the one or more cones comprises:
    manipulating one or more tethers coupled with the one or more cones to move the one or more cones with respect to the ablation structure.

18. The method of claim 13, wherein the one or more support elements comprises one or more bumpers coupled with one or more edges of the ablation structure.

19. The method of claim 13, wherein the one or more support elements proximal to the ablation structure comprises a raised bump coupled with the catheter.

20. The method of claim 13, wherein the one or more support elements distal to the ablation structure comprises a bunched up portion of the expansion member configured to bunch up when the expansion member is in the furled configuration.

* * * * *